(12) United States Patent
Buzard et al.

(10) Patent No.: US 7,956,071 B2
(45) Date of Patent: Jun. 7, 2011

(54) IMIDAZOLE COMPOUNDS

(75) Inventors: Daniel J. Buzard, San Diego, CA (US); James P. Edwards, San Diego, CA (US); David E. Kindrachuk, Cardiff by the Sea, CA (US); Jennifer D. Venable, Solana Beach, CA (US)

(73) Assignee: Janssen Pharmaceutica NV, Beerse (BE)

( * ) Notice: Subject to any disclaimer, the term of this patent is extended or adjusted under 35 U.S.C. 154(b) by 516 days.

(21) Appl. No.: 11/704,112

(22) Filed: Feb. 8, 2007

(65) Prior Publication Data

US 2007/0173512 A1 Jul. 26, 2007

Related U.S. Application Data

(62) Division of application No. 11/088,488, filed on Mar. 24, 2005, now Pat. No. 7,253,200.

(60) Provisional application No. 60/556,356, filed on Mar. 25, 2004.

(51) Int. Cl.
*C07D 211/44* (2006.01)
*A01N 43/40* (2006.01)
*A61K 31/44* (2006.01)

(52) U.S. Cl. ........ 514/345; 514/314; 546/184; 546/216; 546/218

(58) Field of Classification Search .................. 546/184, 546/216, 218; 514/315, 345, 314
See application file for complete search history.

(56) References Cited

FOREIGN PATENT DOCUMENTS

WO WO 2004/016611 12/2004
WO WO 2005/044807 A1 5/2005

OTHER PUBLICATIONS

Wolff, M.E., "Burger's Medicinal Chemistry", 5th Ed., Part 1, pp. 975-977 (1995).*
Banker et al., "Modern Pharmaceuticals", 3rd Ed., p. 596 (1996).*
Arrang, J.-M. et al. Auto-inhibition of Brain Histamine Release Mediated by a Novel Class ($H_3$) of Histamine Receptor. Nature (1983) 302:832-837.
Ash, A.S.F.; Schild, H.O. Receptors Mediating Some Actions of Histamine. Br. J. Pharmac. Chemother. (1966) 27:427-439.
Barger, G.; Dale, H.H. Chemical Structure and Sympathomimetic Action of Amines. J. Physiol. (1910) 41:19-59 Reprinted in Adventures in Physiology; Sir Henry H. Dale, Ed.; The Wellcome Trust: London, 1965; pp. 67-98.
Benoist, C. et al. Mast Cells in Autoimmune Disease. Nature (2002) 420(6917):875-878.
Berge, S.M. et al. Pharmaceutical Salts. J. Pharm. Sci. 1977, 66(1), 1-19.
Black, J.W. et al. Definition and Antagonism of Histamine H2-Receptors. Nature (1972) 236:385-390.
Cohen, J. The Immunopathogenesis of Sepsis. Nature (2002) 420(6917):885-891.
Coussens, L.M. et al. Inflammation and Cancer. Nature (2002) 420(6917):860-867.
Gantz, I. et al. Molecular Cloning of a Gene Encoding the Histamine H2 Receptor. Proc. Natl. Acad. Sci. USA (1991) 88(2):429-433.
Hill, S.J. et al. International Union of Pharmacology. XIII. Classification of Histamine Receptors. Pharmacol. Rev. (1997) 49(3):253-278.
Hofstra, C.L. et al. Histamine $H_4$ Receptor Mediates Chemotaxis and Calcium Mobilization of Mast Cells. J. Pharmacol. Exp. Ther. (2003) 305(3):1212-1221.
Larock, R.C. Comprehensive Organic Transformations; VCH Publishers: New York, 1989; pp. 397-400, 421-425.
Lee et al., N-H Insertion Reactions of Primary Ureas: The synthesis of Highly Substituted Imidazolones and Imidasoles from Ciaocarbonyls, JOC Article, J. Org. Chem. 2004, vol. 69, pp. 8829-8835.
Libby, P. Inflammation in Atherosclerosis. Nature (2002) 420(6917):868-874.
Liu, C. et al. Cloning and Pharmacological Characterization of a Fourth Histamine Receptor ($H_4$) Expressed in Bone Marrow. Mol. Pharmacol. (2001) 59(3):420-426.
Lovenberg, T.W. et al. Cloning and Functional Expression of the Human Histamine $H_3$ Receptor. Mol. Pharmacol. (1999) 55(6):1101-1107.
March, J. Advanced Organic Chemistry, 4th ed.; John Wiley & Sons: New York, 1991; pp. 411-412, 1200-1201.
Morse, K.L. et al. Cloning and Characterization of a Novel Human Histamine Receptor. J. Pharmacol. Exp. Ther. (2001) 296(3):1058-1066.
Nathan, C. Points of Control in Inflammation. Nature (2002) 420(6917):846-852.
Nguyen, T. et al. Discovery of a Novel Member of the Histamine Receptor Family. Mol. Pharmacol. (2001) 59(3):427-433.
Oda, T. et al. Molecular Cloning and Characterization of a Novel Type of Histamine Receptor Preferentially Expressed in Leukocytes. J. Biol. Chem. (2000) 275(47):36781-36786.
Raible, D.G. et al. Pharmacologic Characterization of a Novel Histamine Receptor on Human Eosinophils. Am. J. Respir. Crit. Care Med. (1994) 149:1506-1511.
Schneider, E. et al. Trends in Histamine Research: New Functions During Immune Responses and Hematopoiesis. Trends Immunol. (2002) 23(5):255-263.
Stark, H. Recent Advances in Histamine $H_3/H_4$ Receptor Ligands. Expert Opin. Ther. Patents (2003) 13(6):851-865.
Steinberg, D. Atherogenesis in Perspective: Hypercholesterolemia and Inflammation as Partners in Crime. Nature Med. (2002) 8(11):1211-1217.
Tracey, K.J. The Inflammatory Reflex. Nature (2002) 420(6917):853-859.
Weiner, H.L. et al. Inflammation and Therapeutic Vaccination in CNS Diseases. Nature (2002) 420(6917):879-884.
Yamashita, M. et al. Expression Cloning of a cDNA Encoding the Bovine Histamine $H_1$ Receptor. Proc. Natl. Acad. Sci. USA (1991) 88(24):11515-11519.
Zhu, Y. et al. Cloning, Expression, and Pharmacological Characterization of a Novel Human Histamine Receptor. Mol. Pharmacol. (2001) 59(3):434-441.
European Supplemental Search Report dated Jun. 6, 2009 for International Appln. No. PCT/US2005/009715.

* cited by examiner

*Primary Examiner* — Paul V. Ward

(57) ABSTRACT

Imidazole compounds, compositions, and methods of using them in leukocyte recruitment inhibition, in modulating $H_4$ receptor expression, and in treating conditions such as inflammation, $H_4$ receptor-mediated conditions, and related conditions.

34 Claims, No Drawings

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: Histamine H4 receptor primer 1

<400> SEQUENCE: 1
```

```
atgccagata ctaatagcac a                                            21

<210> SEQ ID NO 2
<211> LENGTH: 19
<212> TYPE: DNA
<213> ORGANISM: Artificial
<220> FEATURE:
<223> OTHER INFORMATION: Histamine H4 receptor primer 2

<400> SEQUENCE: 2
cagtcggtca gtatcttct                                               19
```

IMIDAZOLE COMPOUNDS

This application is a divisional of U.S. patent application Ser. No. 11/088,488, filed on Mar. 24, 2005 now U.S. Pat. No. 7,253,200, which in turn claims the benefit of U.S. provisional patent application Ser. No. 60/556,356, filed on Mar. 25, 2004, each of which is incorporated herein by reference in its entirety.

FIELD OF THE INVENTION

The invention relates to novel, pharmaceutically active, heterocyclic compounds, more particularly imidazole compounds, and methods of using them to treat or prevent disorders and conditions mediated by the histamine $H_4$ receptor.

BACKGROUND OF THE INVENTION

Histamine was first identified as a hormone (Barger, G. and H. H. Dale, *J. Physiol.* (*London*) 1910, 41:19-59) and has since been demonstrated to play a major role in a variety of physiological processes, including the inflammatory "triple response" via $H_1$ receptors (Ash, A. S. F. and H. O. Schild, *Br. J. Pharmac. Chemother.* 1966, 27:427-439), gastric acid secretion via $H_2$ receptors (Black, J. W. et al., *Nature* 1972, 236:385-390), and neurotransmitter release in the central nervous system via $H_3$ receptors (Arrang, J.-M. et al., *Nature* 1983, 302:832-837) (for review see Hill, S. J. et al., *Pharmacol. Rev.* 1997, 49(3):253-278). All three histamine receptor subtypes have been demonstrated to be members of the superfamily of G protein-coupled receptors (Gantz. I. et al., *Proc. Natl. Acad. Sci. U.S.A.* 1991, 88:429-433; Lovenberg, T. W. et al., *Mol. Pharmacol.* 1999, 55(6):1101-1107; Yamashita, M. et al., *Proc. Natl. Acad. Sci. U.S.A.* 1991, 88:11515-11519). There are, however, additional functions of histamine that have been reported, for which no receptor has been identified. For example, in 1994, Raible et al. demonstrated that histamine and R-α-methylhistamine could activate calcium mobilization in human eosinophils (Raible, D. G. et al., *Am. J. Respir. Crit. Care Med.* 1994, 149:1506-1511). These responses were blocked by the $H_3$-receptor antagonist thioperamide. However, R-α-methylhistamine was significantly less potent than histamine, which was not consistent with the involvement of known $H_3$ receptor subtypes. Therefore, Raible et al. hypothesized the existence of a novel histamine receptor on eosinophils that was non-$H_1$, non-$H_2$, and non-$H_3$. Most recently several groups (Oda, T. et al., *J. Biol. Chem.* 2000, 275(47):36781-36786; Liu, C. et al., *Mol. Pharmacol.* 2001, 59(3):420-426; Nguyen, T. et al., *Mol. Pharmacol.* 2001, 59(3):427-433; Zhu, Y. et al., *Mol. Pharmacol.* 2001, 59(3):434-441; Morse, K. L. et al., *J. Pharmacol. Exp. Ther,* 2001, 296(3):1058-1066) have identified and characterized a fourth histamine receptor subtype, the $H_4$ receptor. This receptor is a 390 amino acid, seven-transmembrane, G protein-coupled receptor with approximately 40% homology to the histamine $H_3$ receptor. In contrast to the $H_3$ receptor, which is primarily located in the brain, the $H_4$ receptor is expressed at greater levels in eosinophils and mast cells, among other cells, as reported by Liu et al. (infra) and Hofstra et al. (*J. Pharmacol. Exp. Ther.* 2003, 305(3):1212-1221). Because of its preferential expression on immunocompetent cells, this $H_4$ receptor is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast-cell de-granulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast-cell activation initiates allergic ($H_1$) inflammatory responses, which in turn cause the recruitment of other effector cells that further contribute to the inflammatory response. The histamine $H_2$ receptors modulate gastric acid secretion, and the histamine $H_3$ receptors affect neurotransmitter release in the central nervous system.

Modulation of $H_4$ receptors controls the release of inflammatory mediators and inhibits leukocyte recruitment, thus providing the ability to prevent and/or treat $H_4$-mediated diseases and conditions, including the deleterious effects of allergic responses such as inflammation. Compounds according to the present invention have $H_4$ receptor modulating properties. Compounds according to the present invention have leukocyte recruitment inhibiting properties. Compounds according to the present invention have anti-inflammatory properties.

Examples of textbooks on the subject of inflammation include Gallin, J. I. and R. Snyderman, *Inflammation: Basic Principles and Clinical Correlates,* 3$^{rd}$ Edition, (Lippincott Williams & Wilkins, Philadelphia, 1999); V. Stvrtinova, V. et al., "Inflammation and Fever", *Pathophysiology Principles of Diseases* (Textbook for Medical Students, Academic Press, 1995); Cecil et al., *Textbook Of Medicine,* 18$^{th}$ Edition (W.B. Saunders Company, 1988); and Steadmans Medical Dictionary.

Background and review material on inflammation and conditions related with inflammation can be found in articles such as the following: Nathan, C. *Nature* 2002, 420;846-852; Tracey, K. J. *Nature* 2002, 420:853-859; Coussens, L. M. and Z. Werb, *Nature* 2002, 420:860-867; Libby, P. *Nature* 2002, 420:868-874; Benoist, C. and D. Mathis, *Nature* 2002, 420: 875-878; Weiner, H. L. and D. J. Selkoe, *Nature* 2002, 420: 879-884; Cohen, J. *Nature* 2002, 420:885-891; Steinberg, D. *Nature Medicine* 2002, 8(11):1211-1217.

Inflammation herein refers to the response that develops as a consequence of histamine release, which in turn is caused by at least one stimulus. Examples of such stimuli are immunological stimuli and non-immunological stimuli.

Inflammation is due to any one of a plurality of conditions such as allergy, asthma, chronic obstructed pulmonary disease (COPD), atherosclerosis, rheumatoid arthritis, multiple sclerosis, inflammatory bowel diseases (including Crohn's disease and ulcerative colitis), psoriasis, allergic rhinitis, scleroderma, autoimmune thyroid diseases, immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, and Sjogren's syndrome. Regarding the onset and evolution of inflammation, inflammatory diseases or inflammation-mediated diseases or conditions include, but are not limited to, acute inflammation, allergic inflammation, and chronic inflammation.

Cited references are incorporated herein by reference.

SUMMARY OF THE INVENTION

The invention features a compound of formula (I) or (II):

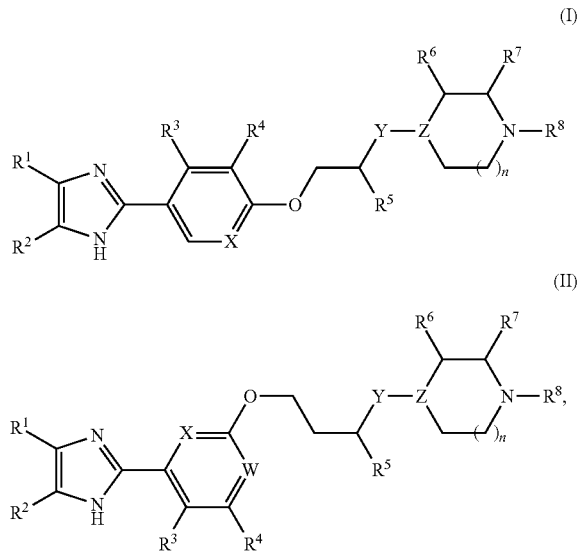

wherein

W is, independently from other member and substituent assignments, N or $CR^9$;

X is, independently from other member and substituent assignments, N or $CR^9$;

Y is, independently from other member and substituent assignments, O, $NR^{10}$, or $CR^{10}R^{11}$;

Z is, independently from other member and substituent assignments, N or $CR^{12}$;

n is, independently from other member and substituent assignments, 0, 1, or 2;

each of $R^{1-2}$ is, independently from other member and substituent assignments, —H, —$CF_3$, —$C_{1-6}$alkyl, —$C_{3-6}$cycloalkyl, optionally substituted aryl or optionally substituted heteroaryl; or, $R^1$ and $R^2$ taken together with the carbon atoms to which they are attached form a cyclic structure Cyc1 selected from 5- or 6-membered carbocycle, and 5- or 6-membered heterocycle with 1 heteroatom, wherein said cyclic structure Cyc1 is, independently from other substituent assignments, substituted with 0, 1, or 2 substituents selected from —$C_{1-3}$alkyl, halo, hydroxy, amino, and —$C_{1-3}$alkoxy;

each of $R^{3-4}$ and $R^9$ is, independently from other member and substituent assignments, —H, —$C_{1-6}$alkyl, halo, —$CF_3$, —$OCF_3$, —$OR^c$, —$SR^c$, —$S(O)R^c$, —$SO_2R^c$, $C_{1-4}$alkoxy, cyano, nitro, —$C(O)NR^aR^b$, —$C(O)$phenyl, —$C(O)C_{1-6}$alkyl, —$S(O)C_{1-4}$alkyl, or —$SO_2C_{1-4}$alkyl; or, $R^3$ and $R^4$ taken together with the carbon atoms to which they are attached form a cyclic structure Cyc2 selected from aryl, 5- or 6-membered carbocycle, and 5- or 6-membered heterocycle with 1 or 2 heteroatoms, wherein said cyclic structure Cyc2 is, independently from other substituent assignments, substituted with 0, 1, or 2 substituents selected from —$C_{1-3}$alkyl, halo, hydroxy, amino, and —$C_{1-3}$alkoxy;

wherein each of $R^a$, $R^b$ and $R^c$ is, independently from other substituent assignments, selected from H, $C_{1-4}$alkyl, $C_{3-6}$cycloalkyl, phenyl, ($C_{3-6}$cycloalkyl)$C_{1-2}$alkyl-, benzyl and phenethyl, or $R^a$ and $R^b$ taken together with the nitrogen to which they are attached, form a 4-7 membered heterocyclic ring HetCyc1, wherein said ring HetCyc1 has 0 or 1 additional heteroatoms selected from O, S, >NH and >$NC_{1-6}$alkyl, and wherein any phenyl, phenethyl, benzyl, alkyl or cycloalkyl moiety in any of said $R^{1-4}$, $R^a$, $R^b$, $R^c$, and said ring HetCyc1 is optionally, and independently from other substituent assignments, substituted with 1, 2 or 3 substituents selected from $C_{1-3}$alkyl, halo, hydroxy, amino, and $C_{1-3}$alkoxy;

$R^5$ is, independently from other member and substituent assignments, —H, —$C_{1-6}$alkyl, —$C_{1-4}$alkoxy, or hydroxy;

each of $R^6$ and $R^7$ is, independently from other member and substituent assignments, —H or —$C_{1-6}$alkyl, or $R^6$ and $R^7$ taken together form a 5-6 membered cyclic structure Cyc3, wherein said cyclic structure Cyc3 is a 5- or 6-membered carbocycle or a 5- or 6-membered heterocycle with 1 or 2 heteroatoms, and wherein said cyclic structure Cyc3 is, independently from other substituent assignments, substituted with 0, 1, or 2 substituents selected from —$C_{1-3}$alkyl, halo, hydroxy, amino, and —$C_{1-3}$alkoxy;

$R^8$ is, independently from other member and substituent assignments, —H or —$C_{1-4}$alkyl;

each of $R^{10}$ and $R^{11}$ is, independently from other member and substituent assignments, —H or —$C_{1-4}$alkyl; or, when Y is $CR^{10}R^{11}$, $R^{10}$ and $R^{11}$ taken together with the carbon member to which they are attached form an optionally substituted cyclic structure Cyc4, wherein said cyclic structure Cyc4 is a 3- to 6-membered carbocycle or a 3- to 6-membered non-aromatic heterocycle with 0 or 1 additional heteroatoms, or $CR^{10}R^{11}$ is C=O;

$R^{12}$ is, independently from other member and substituent assignments, —H, —$C_{1-4}$alkyl, hydroxy, or —$C_{1-4}$alkoxy;

and enantiomers, diastereomers, racemates, tautomers, hydrates, solvates thereof, and pharmaceutically acceptable salts, amides or esters thereof; with the following provisos:

when Y is O or $NR^{10}$, then Z is $CR^{12}$ and $R^5$ is not hydroxy or —$C_{1-4}$alkoxy;

when Z is N, Y is $CR^{10}R^{11}$;

when $R^1$ and $R^2$ are both —H, Y is $CH_2$, and $R^8$ is methyl, then $R^5$ is not hydroxy.

Embodiments of compounds of formulae (I) and (II) are modulators of the $H_4$ receptor. Embodiments of this invention comprise mixtures of compounds of formulae (I) and (II).

Isomeric forms of the compounds of formulae (I) and (II), and of their pharmaceutically acceptable salts, amides and esters, are encompassed within the present invention, and reference herein to one of such isomeric forms is meant to refer to at least one of such isomeric forms. One of ordinary skill in the art will recognize that compounds according to this invention may exist, for example, in a single isomeric form whereas other compounds may exist in the form of a regioisomeric mixture.

Whether stated explicitly or not in any part of the written description and claims, it is understood that each substituent and member assignment in the context of this invention is made independently of any other member and substituent assignment, unless stated otherwise. By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent R assignments described herein. The foregoing convention given herein for substituents extends, when applicable, to members such as X, Y, Z, and W, and the index n.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent R assignments described herein. The foregoing convention given herein for substituents extends, when applicable, to members such as X, Y, Z, and W, and the index n.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≦N≦m, with m>n.

When any variable referring to a substituent, compound member or index, occurs more than once, the full range of assignments is meant to apply to each occurrence, independently of the specific assignment(s) to any other occurrence of such variable. For each occurrence of a variable, it is understood that such an assignment is made independently from other member and substituent assignments.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

The present invention also features methods for inhibiting $H_4$ receptor activity with such compounds, pharmaceutical compositions containing such compounds, and methods of using such compositions in the treatment or prevention of conditions that are mediated by the $H_4$ receptor, such as inflammation. Compounds according to the present invention and derivatives thereof can also be used as reference compounds in assays to assess $H_4$ receptor modulating characteristics in light of one or more factors such as receptor inhibition, toxicity, bioavailability, and protein binding capability.

Pharmaceutical compositions according to the present invention include at least one of the compounds of the present invention. If more than one of such compounds is included in a composition, the therapeutically effective amount may be a jointly effective amount. As such inhibitors of $H_4$ receptor activity, compounds and compositions according to the present invention are useful in the prevention, inhibition, or treatment of $H_4$ receptor-mediated conditions, such as inflammation.

The invention also features a pharmaceutical composition for treating or preventing an $H_4$ receptor-mediated condition in a subject, comprising a therapeutically effective amount of at least one $H_4$ receptor modulator selected from compounds of formulae (I) and (II), enantiomers, diastereomers, racemates, tautomers, hydrates, solvates thereof, pharmaceutically acceptable salts, amides and esters thereof. In addition, the invention features a pharmaceutical composition for inhibiting leukocyte recruitment in a subject, comprising a therapeutically effective amount of at least one leukocyte recruitment inhibitor selected from compounds of formulae (i) and (II), enantiomers, diastereomers, racemates, tautomers, hydrates, solvates thereof, pharmaceutically acceptable salts, amides and esters thereof. The invention additionally features an anti-inflammatory composition, comprising a therapeutically effective amount of at least one anti-inflammatory compound selected from compounds of formulae (I) and (II), enantiomers, diastereomers, racemates, tautomers, hydrates, solvates thereof, pharmaceutically acceptable salts, amides and esters thereof.

The invention features methods for treating or preventing inflammation in a subject, comprising administering to the subject in connection with an inflammatory response a pharmaceutical composition that comprises a therapeutically effective amount of at least one anti-inflammatory compound selected from compounds of formulae (I) and (II), enantiomers, diastereomers, racemates, tautomers, hydrates, solvates thereof, pharmaceutically acceptable salts, amides and esters thereof. The invention also features methods for treating or preventing an $H_4$ receptor-mediated condition in a subject, comprising administering to the subject a pharmaceutical composition that comprises a therapeutically effective amount of at least one $H_4$ receptor modulator selected from compounds of formulae (I) and (II), enantiomers, diastereomers, racemates, tautomers, hydrates, solvates thereof, pharmaceutically acceptable salts, amides and esters thereof. In addition, the invention features methods for modulating an $H_4$ receptor expression, comprising exposing an $H_4$ receptor to at least one compound selected from compounds of formulae (I) and (II), enantiomers, diastereomers, racemates, tautomers, hydrates, solvates thereof, pharmaceutically acceptable salts, amides and esters thereof. Furthermore, the invention features methods for inhibiting leukocyte recruitment in a subject, comprising administering to the subject a pharmaceutical composition that comprises a therapeutically effective amount of at least one leukocyte recruitment inhibitor selected from compounds of formulae (I) and (II), enantiomers, diastereomers, racemates, tautomers, hydrates, solvates thereof, pharmaceutically acceptable salts, amides and esters thereof.

DETAILED DESCRIPTION

The present invention is directed to compounds of formulae (I) or (II) as herein defined, enantiomers, diastereomers, racemates, tautomers, hydrates, solvates thereof, pharmaceutically acceptable salts, amides and esters thereof, pharmaceutical compositions that contain at least one of such compounds, methods of using, including treatment and/or prevention of conditions such as those that are mediated by the $H_4$ receptor, and methods of making such pharmaceutical compositions.

The following terms are defined below, and by their usage throughout the disclosure.

"Alkyl" includes straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl does not include cycloalkyl.

"Alkenyl" includes straight chain and branched hydrocarbon radicals as above with at least one carbon-carbon double bond ($sp^2$). Unless indicated otherwise by the prefix that indicates the number of carbon members, alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on.

"Alkynyl" includes straight chain and branched hydrocarbon radicals as above with at least one carbon-carbon triple bond (sp). Unless indicated otherwise by the prefix that indicates the number of carbon members, alkynyls include ethynyl, propynyls, butynyls, and pentynyls. Hydrocarbon radicals having a mixture of double bonds and triple bonds, such as 2-penten-4-ynyl, are grouped as alkynyls herein.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$.

Unless indicated otherwise by the prefix that indicates the number of carbon members, "cycloalkyl" includes cyclopropyl, cyclobutyl, cyclopentyl, cyclohexyl, cycloheptyl, cyclooctyl, and so on.

Unless indicated otherwise by the prefix that indicates the number of members in the cyclic structure, "heterocyclyl", "heterocyclic" or "heterocycle" is a 3- to 8-member aromatic, saturated, or partially saturated single or fused ring system that comprises carbon atoms wherein the heteroatoms are selected from N, O, and S. Examples of heterocyclyls include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imidazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, cycloheptylimino, and more preferably, piperidyl.

Carbocycle is a cycloalkyl or a partially saturated cycloalkyl that is not benzo

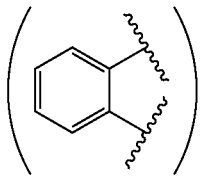

"Aryl" includes phenyl, naphthyl, biphenylyl, tetrahydronaphthyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridged, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on. Unless indicated otherwise, the terms "heteroaryl" or "heteroaromatic" refer to those heterocycles that are aromatic in nature. Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl, pyridyl, and pyrimidinyl.

"Halo" includes fluoro, chloro, bromo, and iodo, and is preferably fluoro or chloro.

When not specifically qualified, the terms "optionally substituted" used herein refer to at least one valence allowed substitution, wherein the substituent(s) is (are) independently selected from the group comprising at least: —$C_{1-6}$alkyl, halo, —$CF_3$, —$OCF_3$, —$OR^c$, —$SR^c$, —$S(O)R^c$, —$SO_2R^c$, $C_{1-4}$alkoxy, cyano, nitro, —$C(O)NR^aR^b$, —$C(O)$phenyl, —$C(O)C_{1-6}$alkyl, —$S(O)C_{1-4}$alkyl, and —$SO_2C_{1-4}$alkyl.

As in standard chemical nomenclature, the group phenyl is herein referred to as "phenyl" or as "Ph".

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum mass of the same entity that could be obtained under the particular stoichiometric conditions. Concentrations that are given as percentages refer to mass ratios, unless indicated differently.

It is understood that substitutions and combinations of substitutions recited herein, whether stated explicitly or not, refer to substitutions that are consistent with the valency of the member being substituted. Terms such as "valence allowed site," "valence allowed member," and morphological variations thereof are used in this sense. For example, "valence allowed" when applied to a carbon member refers to the tetravalency of C; it refers to the trivalency of N when applied to a nitrogen member; and it refers to the bonding of a nitrogen member that is conventionally characterized with a positive electric charge or that is in a quaternary form. The present invention also encompasses compounds as described herein and equivalents thereof with at least one valence allowed nitrogen member, including but not limited to a quaternary nitrogen member and a nitrogen oxide, each of which may be prepared according to known methods (See, J. March, Advanced Organic Chemistry, 4th ed., 1991, pp. 411-412, 1200-1201; R. C. Larock, Comprehensive Organic Transformations, 1989, pp. 397-400, 421-425; and references cited therein).

Particular preferred compounds of the invention comprise an imidazole compound of formula (I) or (II), or an enantiomer, diastereomer, racemate, tautomer, hydrate, solvate thereof, or a pharmaceutically acceptable salt, amide or ester thereof, wherein $R^{1-12}$, X, Y, Z, W, and n have any of the meanings defined hereinabove and equivalents thereof, or at least one of the following assignments and equivalents thereof. Such assignments may be used where appropriate with any of the definitions, claims or embodiments defined herein:

Y is $CR^{10}R^{11}$;
Y is $CH_2$;
Z is N or CH;
n=1 or 2;
n=1;
one or both of $R^1$ and $R^2$ are a mono- or di-substituted phenyl ring;
only one of $R^1$ or $R^2$ is a mono-substituted phenyl ring;
$R^3$ is —H, —F, —Cl, methyl, or ethyl;
$R^3$ is —F, —Cl, or methyl;
$R^3$ is —Cl or methyl;
$R^4$ is —H, —F, —Cl, or methyl;
$R^5$ is —H, methyl, or hydroxy;
$R^5$ is H;
$R^6$ and $R^7$ are, independently, selected from the group consisting of
a) H,
b) methyl, ethyl, propyl, isopropyl, and
c) trifluoromethyl;
$R^6$ and $R^7$ are, independently, —H or methyl;
$R^8$ is —H, methyl, or ethyl;
$R^8$ is methyl; and
$R^9$ is, —H, —F, —Cl, or methyl.

Compounds of formula (I) or (II) comprise compounds that satisfy any one of the combinations of definitions given herein and equivalents thereof.

It is understood that some compounds referred to herein are chiral and/or have geometric isomeric centers, for example E- and Z-isomers. The present invention encompasses all such optical isomers, including diastereoisomers and racemic mixtures, and geometric isomers that possess the activity that characterizes the compounds of this invention. In addition, certain compounds referred to herein can exist in solvated as well as unsolvated forms. It is understood that this invention encompasses all such solvated and unsolvated forms that possess the activity that characterizes the compounds of this invention. Compounds according to the present invention that have been modified to be detectable by some analytic technique are also within the scope of this invention. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Another example of such compounds is an isotopically labeled compound, such as a deuterium and/or tritium labeled compound that may be used in reaction kinetic studies.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound that may not be specifically disclosed, but that converts to the specified compound in vivo after administration to the patient. Conventional procedures for the selection and preparation of suitable prodrug derivatives are described, for example, in "Design of Prodrugs", ed. H. Bundgaard, Elsevier, 1985.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—$COOH_{(s)}$, R—$COOH_{(sol)}$, and R—$COO^-_{(sol)}$. In this example, R—$COOH_{(s)}$ refers to the solid compound, as it could be for example in a tablet or some other solid pharmaceutical composition or preparation; R—$COOH_{(sol)}$ refers to the undissociated form of the compound in a solvent, such as water; and R—$COO^-_{(sol)}$ refers to the dissociated form of the compound in a solvent, such as the dissociated form of the compound in an aqueous environment, whether such dissociated form derives from R—COOH, from a salt thereof, or from any other entity that yields R—$COO^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—$COOH_{(aq)}$ and/or R—$COO^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Embodiments of this invention were made according to the synthetic methods outlined in Schemes 1 and 2 and are selected from:

| EX | Compound |
|---|---|
| 1 | 1-(3-{4-[4,5-Bis-(4-bromo-phenyl)-1H-imidazol-2-yl]-3-chloro-phenoxy}-propyl)-4-methyl-piperazine; |
| 2 | 1-{3-[3-Chloro-4-(4,5-diphenyl-1H-imidazol-2-yl)-phenoxy]-propyl}-4-methyl-piperazine; |
| 3 | 1-(3-{4-[4,5-Bis-(2-chloro-phenyl)-1H-imidazol-2-yl]-3-chloro-phenoxy}-propyl)-4-methyl-piperazine; |

| EX | Compound |
|---|---|
| 4 | 1-(3-{4-[4,5-Bis-(4-methoxy-phenyl)-1H-imidazol-2-yl]-3-chloro-phenoxy}-propyl)-4-methyl-piperazine; |
| 5 | 1-{3-[3-Chloro-4-(4,5-di-p-tolyl-1H-imidazol-2-yl)-phenoxy]-propyl}-4-methyl-piperazine; |
| 6 | 1-(3-{4-[4,5-Bis-(4-fluoro-phenyl)-1H-imidazol-2-yl]-3-chloro-phenoxy}-propyl)-4-methyl-piperazine; |
| 7 | 1-(3-{4-[4,5-Bis-(3-methoxy-phenyl)-1H-imidazol-2-yl]-3-chloro-phenoxy}-propyl)-4-methyl-piperazine; |
| 8 | 1-(3-{4-[4,5-Bis-(3-methoxy-phenyl)-1H-imidazol-2-yl]-2-fluoro-phenoxy}-propyl)-4-methyl-piperazine; |
| 9 | 1-(3-{4-[4,5-Bis-(4-bromo-phenyl)-1H-imidazol-2-yl]-3-chloro-phenoxy}-propyl)-4-methyl-[1,4]diazepane; |
| 10 | 1-(3-{4-[4,5-Bis-(3-methoxy-phenyl)-1H-imidazol-2-yl]-3-chloro-phenoxy}-propyl)-4-methyl-[1,4]diazepane |
| 11 | 1-{3-[2-Chloro-4-(5-methyl-4-phenyl-1H-imidazol-2-yl)-phenoxy]-propyl}-4-methyl-[1,4]diazepane; |
| 12 | 2-{3-Chloro-4-[3-(4-methyl-[1,4]diazepan-1-yl)-propoxy]-phenyl}-4,5,6,7-tetrahydro-1H-benzoimidazole; |
| 13 | 2-{2-Chloro-4-[3-(4-methyl-[1,4]diazepan-1-yl)-propoxy]-phenyl}-4,5,6,7-tetrahydro-1H-benzoimidazole; |
| 14 | 1-Methyl-4-{3-[3-methyl-4-(4-phenyl-5-trifluoromethyl-1H-imidazol-2-yl)-phenoxy]-propyl}-piperidine; |
| 15 | 4-{3-[3-Chloro-4-(4-phenyl-5-trifluoromethyl-1H-imidazol-2-yl)-phenoxy]-propyl}-1-methyl-piperidine; |
| 16 | 4-(3-{3-Chloro-4-[5-methyl-4-(3-trifluoromethyl-phenyl)-1H-imidazol-2-yl]-phenoxy}-propyl)-1-methyl-piperidine; |
| 17 | 4-(3-{3-Chloro-4-[4-(3,5-dichloro-phenyl)-5-methyl-1H-imidazol-2-yl]-phenoxy}-propyl)-1-methyl-piperidine; |
| 18 | 4-(3-{4-[4-(3,5-Dichloro-phenyl)-5-methyl-1H-imidazol-2-yl]-3-methyl-phenoxy}-propyl)-1-methyl-piperidine; |
| 19 | 4-(3-{3-Chloro-4-[4-(4-chloro-phenyl)-5-methyl-1H-imidazol-2-yl]-phenoxy}-propyl)-1-methyl-piperidine; |
| 20 | 4-(3-{4-[4,5-Bis-(4-fluoro-phenyl)-1H-imidazol-2-yl]-3-chloro-phenoxy}-propyl)-1-methyl-piperidine; |
| 21 | 4-(3-{4-[4,5-Bis-(3-methoxy-phenyl)-1H-imidazol-2-yl]-3-chloro-phenoxy}-propyl)-1-methyl-piperidine; |
| 22 | 4-(3-{3-Chloro-4-[4-(4-chloro-phenyl)-5-p-tolyl-1H-midazol-2-yl]-phenoxy}-propyl)-1-methyl-piperidine; |
| 23 | 2-{2-Chloro-4-[3-(1-methyl-piperidin-4-yl)-propoxy]-phenyl}-4,5,6,7-tetrahydro-1H-benzoimidazole; |
| 24 | 4-{3-[3-Chloro-4-(4-methyl-5-propyl-1H-imidazol-2-yl)-phenoxy]-propyl}-1-methyl-piperidine; |
| 25 | 4-{3-[3-Chloro-4-(5-ethyl-4-methyl-1H-imidazol-2-yl)-phenoxy]-propyl}-1-methylpiperidine; |
| 26 | 1-Methyl-4-(2-{3-methyl-4-[5-methyl-4-(3-trifluoromethyl-phenyl)-1H-imidazol-2-yl]-phenoxy}-ethoxy)-piperidine; |
| 27 | 5-[4-(3,5-Dichloro-phenyl)-5-methyl-1H-imidazol-2-yl]-2-[3-(1-methyl-piperidin-4-yl)-propoxy]-pyridine; |
| 28 | 5-[4-(4-Chloro-phenyl)-5-methyl-1H-imidazol-2-yl]-2-[3-(1-methyl-piperidin-4-yl)-propoxy]-pyridine; |
| 29 | 2-[3-(1-Methyl-piperidin-4-yl)-propoxy]-5-[5-methyl-4-(3-trifluoromethyl-phenyl)-1H-imidazol-2-yl]-pyridine; |
| 30 | 2-[3-(1-Methyl-piperidin-4-yl)-propoxy]-5-[5-methyl-4-(4-trifluoromethyl-phenyl)-1H-imidazol-2-yl]-pyridine; |
| 31 | 2-[3-(1-Methyl-piperidin-4-yl)-propoxy]-5-(4-phenyl-5-trifluoromethyl-1H-imidazol-2-yl)-pyridine; |
| 32 | 1-Methyl-4-(3-{5-[5-methyl-4-(4-trifluoromethyl-phenyl)-1H-imidazol-2-yl]-pyridin-2-yloxy}-propyl)-piperazine; |
| 33 | 1-Methyl-4-(3-{5-[5-methyl-4-(3-trifluoromethyl-phenyl)-1H-imidazol-2-yl]-pyridin-2-yloxy}-propyl)-piperazine; |
| 34 | 4-(4-{3-[4-(4-Chloro-phenyl)-5-methyl-1H-imidazol-2-yl]-phenoxy}-butyl)-1-methyl-piperidine; |
| 35 | 1-Methyl-4-{4-[3-(4-phenyl-5-trifluoromethyl-1H-imidazol-2-yl)-phenoxy]-butyl}-piperidine; |
| 36 | 2-[4-(1-Methyl-piperidin-4-yl)-butoxy]-4-(4-phenyl-5-trifluoromethyl-1H-imidazol-2-yl)-pyridine; |
| 37 | 2-[4-(1-Methyl-piperidin-4-yl)-butoxy]-4-[5-methyl-4-(3-trifluoromethyl-phenyl)-1H-imidazol-2-yl]-pyridine; |
| 38 | 4-{3-[4-(5-Isobutyl-4-methyl-1H-imidazol-2-yl)-3-methyl-phenoxy]-propyl}-1-methyl-piperidine; |
| 39 | 4-[4-(4-Chloro-phenyl)-5-methyl-1H-imidazol-2-yl]-2-[4-(1-methyl-piperidin-4-yl)-butoxy]-pyridine; |
| 40 | 4-{3-[3-Chloro-4-(5-isobutyl-4-methyl-1H-imidazol-2-yl)-phenoxy]-propyl}-1-methyl-piperidine; |
| 41 | 1-Methyl-4-(4-{3-[5-methyl-4-(4-trifluoromethyl-phenyl)-1H-imidazol-2-yl]-phenoxy}-butyl)-piperidine; |
| 42 | 1-{3-[2-Chloro-4-(1H-imidazol-2-yl)-phenoxy]-propyl}-4-methyl-piperazine; |
| 43 | 1-{3-[3-Chloro-4-(4,5-dimethyl-1H-imidazol-2-yl)-phenoxy]-propyl}-4-methyl-piperazine; |
| 44 | 1-{3-[3-Chloro-4-(4-phenyl-5-trifluoromethyl-1H-imidazol-2-yl)-phenoxy]-propyl}-4-methyl-piperazine; |
| 45 | 1-{3-[2-Chloro-4-(4-phenyl-5-trifluoromethyl-1H-imidazol-2-yl)-phenoxy]-propyl}-4-methyl-[1,4]diazepane; |
| 46 | 1-Methyl-4-(3-{3-methyl-4-[5-methyl-4-(3-trifluoromethyl-phenyl)-1H-imidazol-2-yl]-phenoxy}-propyl)-piperidine; |
| 47 | 4-(3-{4-[4-(4-Chloro-phenyl)-5-methyl-1H-imidazol-2-yl]-3-methyl-phenoxy}-propyl)-1-methyl-piperidine; |
| 48 | 4-(2-{4-[4-(4-Chloro-phenyl)-5-methyl-1H-imidazol-2-yl]-3-methyl-phenoxy}-ethoxy)-1-methyl-piperidine; |
| 49 | 1-(3-{4-[4-(4-Chloro-phenyl)-5-methyl-1H-imidazol-2-yl]-3-methyl-phenoxy}-2-methyl-propyl)-4-methyl-piperazine; |
| 50 | 2-[4-(4-Chloro-phenyl)-5-methyl-1H-imidazol-2-yl]-6-[4-(1-methyl-piperidin-4-yl)-butoxy]-pyridine; |
| 51 | 4-Methyl-2-[3-(1-methyl-piperidin-4-yl)-propoxy]-5-[5-methyl-4-(3-trifluoromethyl-phenyl)-1H-imidazol-2-yl]-pyridine; |
| 52 | 5-Bromo-4-[4-(4-chloro-phenyl)-5-methyl-1H-imidazol-2-yl]-2-[4-(1-methyl-piperidin-4-yl)-butoxy]-pyridine; |
| 53 | 2,4-Dimethyl-1-{3-[4-(4-phenyl-5-trifluoromethyl-1H-imidazol-2-yl)-phenoxy]-propyl}-piperazine; |
| 54 | 1,2-Dimethyl-4-{3-[4-(4-phenyl-5-trifluoromethyl-1H-imidazol-2-yl)-phenoxy]-propyl}-piperazine; |
| 55 | 3-Chloro-2-[4-(1-methyl-piperidin-4-yl)-butoxy]-4-(4-phenyl-5-trifluoromethyl-1H-imidazol-2-yl)-pyridine; |
| 56 | 1-Methyl-4-(4-{4-[5-methyl-4-(3-trifluoromethyl-phenyl)-1H-imidazol-2-yl]-pyridin-2-yloxy}-butyl)-[1,4]diazepane; |
| 57 | 5-Bromo-2-[4-(1-methyl-piperidin-4-yl)-butoxy]-4-[5-methyl-4-(3-trifluoromethyl-phenyl)-1H-imidazol-2-yl]-pyridine; |
| 58 | 4-[4-(4-Chloro-phenyl)-5-trifluoromethyl-1H-imidazol-2-yl]-2-[4-(1-methyl-piperidin-4-yl)-butoxy]-pyrimidine; |
| 59 | 4-(3-{4-[5-Cyclopropylmethyl-4-(3-trifluoromethyl-phenyl)-1H-imidazol-2-yl]-3-methyl-phenoxy}-propyl)-1-methyl-piperidine; |
| 60 | 1-{4-[4-(4-Chloro-phenyl)-5-methyl-1H-imidazol-2-yl]-3-methyl-phenoxy}-3-(4-methyl-piperazin-1-yl)-propan-2-ol; |
| 61 | 4-(3-{3-Chloro-4-[4-(4-chloro-phenyl)-5-methyl-1H-imidazol-2-yl]-phenoxy}-propyl)-piperidine; |
| 62 | 4-(3-{3-Chloro-4-[4-(4-chloro-phenyl)-5-methyl-1H-imidazol-2-yl]-phenoxy}-propyl)-1-ethyl-piperidine; |
| 63 | 4-(3-{3-Chloro-4-[4-(4-chloro-phenyl)-5-methyl-1H-imidazol-2-yl]-phenoxy}-propyl)-1-isopropyl-piperidine; |
| 64 | 1-Methyl-4-{3-[4-(4-phenyl-5-trifluoromethyl-1H-imidazol-2-yl)-naphthalen-1-yloxy]-propyl}-piperidine; |
| 65 | 1-(4-Methyl-piperazin-1-yl)-3-{5-[5-methyl-4-(4-trifluoromethyl-phenyl)-1H-imidazol-2-yl]-pyridin-2-yloxy}-propan-1-one; |
| 66 | 6-[4-(4-Chloro-phenyl)-5-methyl-1H-imidazol-2-yl]-3-fluoro-2-[4-(1-methyl-piperidin-4-yl)-butoxy]-pyridine; |
| 67 | 1-Methyl-4-(4-{3-methyl-6-[5-methyl-4-(3-trifluoromethyl-phenyl)-1H-imidazol-2-yl]-pyridin-2-yloxy}-butyl)-piperazine; |
| 68 | 1-Methyl-4-{3-[4-(5-methyl-4-thiophen-2-yl-1H-imidazol-2-yl)-phenoxy]-propyl}-piperidine; and |
| 69 | 2-{3-[4-(1-Methyl-piperidin-4-yl)-butoxy]-phenyl}-3H-imidazo[4,5-b]pyridine. |

Compounds according to the present invention may be made according to processes within the skill of the art and/or according to processes of this invention, such as those described in the schemes and examples that follow and by matrix or combinatorial methods. To obtain the various compounds herein, starting materials may be employed that carry the ultimately desired substituents though the reaction scheme with or without protection as appropriate. Starting materials may be obtained from commercial sources or synthesized by methods known to one skilled in the art. Alternatively, it may be necessary to employ, in the place of the ultimately desired substituent, a suitable group, which may be carried through the reaction scheme and replaced as appropriate with the desired substituent. Those of ordinary skill in the art will be able to modify and adapt the guidance provided herein to make compounds according to the present invention.

Embodiments of processes illustrated herein include, when chemically meaningful, one or more steps such as hydrolysis, halogenation, protection, and deprotection. These steps can be implemented in light of the teachings provided herein and the ordinary skill in the art.

During any of the processes for preparation of the compounds of the present invention, it may be necessary and/or desirable to protect sensitive or reactive groups on any of the molecules concerned. In addition, compounds of this invention may be modified by using protecting groups; such compounds, precursors, or prodrugs are also within the scope of the invention. This modification may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", 3$^{rd}$ ed., John Wiley & Sons, 1999. The protecting groups may be removed at a convenient subsequent stage using methods known from the art.

| Table of Acronyms | |
|---|---|
| Term | Acronym |
| Tetrahydrofuran | THF |
| N,N-Dimethylformamide | DMF |
| N,N-Dimethylacetamide | DMA |
| Dimethyl sulfoxide | DMSO |
| tert-Butylcarbamoyl | BOC |
| Bovine serum albumin | BSA |
| High-pressure liquid chromatography | HPLC |
| Thin layer chromatography | TLC |
| Diisobutylaluminum hydride | DIBAL-H |
| Ethyl acetate | EtOAc |
| Acetate | OAc |

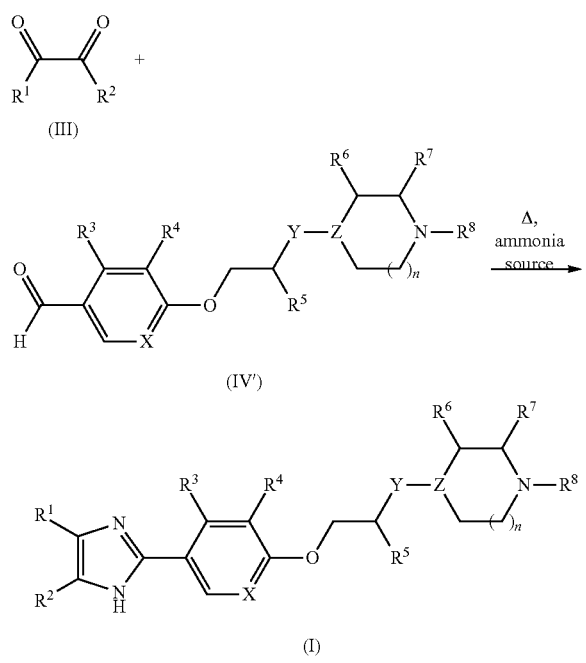

SCHEME 1

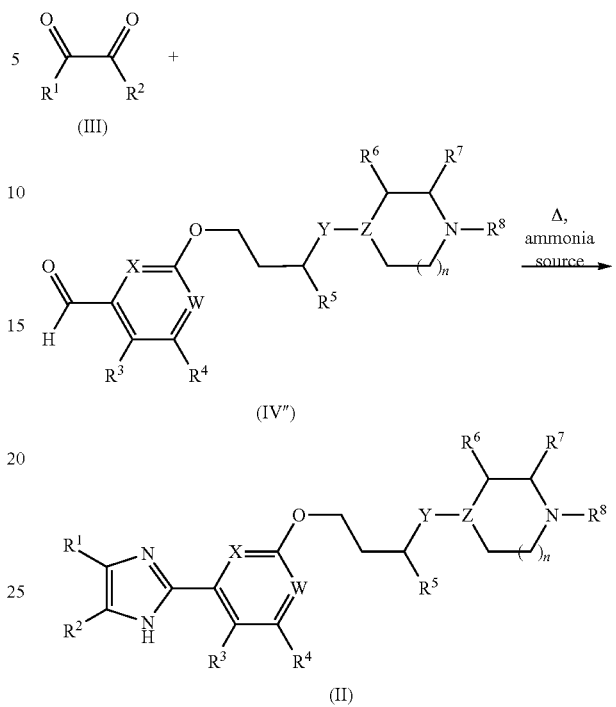

SCHEME 2

Referring to Schemes 1 and 2, there are disclosed the following notes and additions. The starting materials for the steps described below regarding Schemes 1 and 2 are commercially available or easily accessible to those skilled in the art.

Compounds of formula (I) or (II) are prepared by condensing a suitably substituted 1,2-diketone (III) with a suitably substituted aldehyde (IV') or (IV") in the presence of a source of ammonia ($NH_3$) to form a compound of formula (I) when the aldehyde (IV') has a para ether substitution with respect to the aldehyde group (Scheme 1), or a compound of formula (II) when the aldehyde (IV") has a meta ether substitution with respect to the aldehyde group (Scheme 2). Suitable sources of ammonia include liquid and gaseous ammonia, aqueous ammonia, ammonia in methyl or ethyl alcohol, ammonia in 1,4-dioxane, $NH_4OAc$, $NH_4Cl$, $NH_4HCO_3$, $(NH_4)_2CO_3$, ammonium benzoate, and other chemically compatible sources of ammonia or ammonium salts, and mixtures thereof.

This condensation is preferably performed in a heated medium in a chemically compatible solvent. Reaction medium temperatures range preferably from about room temperature to about 110° C., more preferably from about 50° C. to about 80° C. Solvents that can be used for this reaction include ethanol, isopropanol, acetic acid, water, THF, dioxane, DMF, DMA, and DMSO, preferably methanol, and mixtures thereof.

Suitably substituted aryl or heteroaryl aldehydes (IV') and (IV") can be prepared according to procedures known in the art. In one preparation procedure, a suitably substituted hydroxy benzaldehyde is reacted with a suitably substituted moiety to form the ether link in compounds (IV') and (IV"). Reaction with a suitably substituted 4-hydroxy benzaldehyde leads to the formation of compound (IV'), and reaction with a suitably substituted 3-hydroxy benzaldehyde leads to the formation of compound (IV").

Where the processes for the preparation of the compounds according to the invention give rise to mixture of stereoisomers, these isomers may be separated by conventional techniques such as resolution, for example by formation of diastereomeric salts, kinetic resolution including variants thereof, such as dynamic resolution, preferential crystallization, biotransformation, enzymatic transformation, and preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be separated using a chiral HPLC column. Regioisomeric mixtures may also be separated into their constituent regioisomers by conventional techniques.

For therapeutic use, salts of the compounds of the present invention are those that are pharmaceutically acceptable. However, salts of acids and bases that are non-pharmaceutically acceptable may also find use, for example, in the preparation or purification of a pharmaceutically acceptable compound. All salts, whether pharmaceutically acceptable or not are included within the ambit of the present invention.

Pharmaceutically acceptable salts, esters, and amides of compounds according to the present invention refer to those salts, amides and ester forms of the compounds of the present invention that would be apparent to the pharmaceutical chemist, i.e., those that are non-toxic and that would favorably affect the pharmacological properties of said compounds of the present invention. Those compounds having favorable pharmacological properties would be apparent to the pharmaceutical chemist, i.e., those that are non-toxic and that possess such pharmacological properties to provide sufficient palatability, absorption, distribution, metabolism and excretion. Other factors, more practical in nature, that are also important in the selection are cost of raw materials, ease of crystallization, yield, stability, hygroscopicity, and flowability of the resulting bulk drug.

Examples of acids that may be used in the preparation of pharmaceutically acceptable salts include the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyariic acid, p-toluenesulfonic acid and undecylenic acid.

Compounds of the present invention containing acidic protons may be converted into their therapeutically active non-toxic metal or amine addition salt forms by treatment with appropriate organic and inorganic bases. Appropriate base salt forms comprise, for example, the ammonium salts; the alkali and earth alkaline metal salts (e.g. lithium, sodium, potassium, magnesium, calcium salts, which may be prepared by treatment with, for example, magnesium hydroxide, calcium hydroxide, potassium hydroxide, zinc hydroxide, or sodium hydroxide); and amine salts made with organic bases (e.g. primary, secondary and tertiary aliphatic and aromatic amines such as L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine). See, e.g., S. M. Berge, et al., "Pharmaceutical Salts", J. Pharm. Sci., 1977, 66:1-19, which is incorporated herein by reference.

"Salt" also comprises the hydrates and solvent addition forms that compounds of the present invention are able to form. Examples of such forms are hydrates, alcoholates, and generally solvates.

Examples of suitable esters include $C_{1-7}$alkyl, $C_{5-7}$cycloalkyl, phenyl, substituted phenyl, and phenyl$C_{1-6}$alkyl-esters. Preferred esters include methyl esters. Furthermore, examples of suitable esters include such esters where one or more carboxyl substituents is replaced with p-methoxybenzyloxy-carbonyl, 2,4,6-trimethylbenzyloxycarbonyl, 9-anthryloxycarbonyl, $CH_3SCH_2COO$—, tetrahydrofur-2-yloxycarbonyl, tetrahydropyran-2-yloxy-carbonyl, fur-2-yloxycarbonyl, benzoylmethoxycarbonyl, p-nitrobenzyloxycarbonyl, 4-pyridylmethoxycarbonyl, 2,2,2-trichloroethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxycarbonyl, 2-benzyloxyphenyloxycarbonyl, 4-methylthiophenyloxycarbonyl, or tetrahydropyran-2-yloxycarbonyl.

Whether referred to herein explicitly or not, each of the terms "pharmaceutically acceptable salts," "pharmaceutically acceptable esters," and "pharmaceutically acceptable amides" include those salts, esters and amides, respectively that do not change the intrinsic properties of the active ingredient. See, for example, Remington, The Science and Practice of Pharmacy, 704 ($20^{th}$ ed., 2000).

"Patient" or "subject" includes mammals such as human beings and animals (e.g., dogs, cats, horses, rats, rabbits, mice, non-human primates) in need of observation, experiment, treatment or prevention in connection with the relevant disease or condition. Preferably, the patient is a human being.

"Composition" includes a product comprising the specified ingredients in the specified amounts, including in the effective amounts, as well as any product that results directly or indirectly from combinations of the specified ingredients in the specified amounts.

Administration of at least one compound of formulae (I) and (II) and/or derivative thereof refers to the administration of such compound in a suitable administration form, whether as such compound itself or as part of a suitable pharmaceutical composition.

"Therapeutically effective amount" or "effective amount" and grammatically related terms mean that amount of active compound or pharmaceutical agent that elicits the biological or medicinal response in an in vitro system, a tissue system, an animal or human being, that is being sought by a researcher, veterinarian, medical doctor, or other clinician, where the medicinal response includes, but is not limited to, alleviation of the symptoms of the disease or disorder being treated. Analogously, terms such as "inhibitory amount", "anti-inflammatory amount," "prophylactically effective amount" and grammatically related terms refer to the amount of active compound or pharmaceutical agent that elicits the response being referred to, such as inhibition and anti-inflammatory effect, respectively, in the system being studied, whether an in vitro system, an animal or a human being that is sought by a researcher, veterinarian, medical doctor, or other clinician, where the medicinal response includes, but is not limited to, alleviation of the symptoms of the disease or disorder being treated.

As used herein, "treating" a disorder, and grammatically related terms, mean eliminating or otherwise ameliorating the cause and/or effects thereof. Terms such as to "inhibit", and grammatically related terms, the onset of a disorder or event, and to "prevent" a disorder or condition, and grammatically related terms, mean preventing, delaying or reducing the likelihood of such onset.

The terms "unit dose" and their grammatical equivalent forms are used herein to refer to physically discrete units suitable as unitary dosages for human patients and other animals, each unit containing a predetermined effective, pharmacologic amount of the active ingredient calculated to produce the desired pharmacological effect. The specifications for the novel unit dosage forms of this invention are determined by, and are directly dependent on, the characteristics of the active ingredient, and on the limitations inherent in the art of compounding such an active ingredient for therapeutic use in humans and other animals.

Embodiments of pharmaceutical compositions for treating or preventing an $H_4$ receptor-mediated condition in a subject that comprise a therapeutically effective amount of at least one $H_4$ receptor modulator selected from compounds of formulae (I) and (II), enantiomers, diastereomers, racemates, tautomers, hydrates, solvates thereof, pharmaceutically acceptable salts, amides and esters thereof, further comprise a pharmaceutically acceptable carrier.

Embodiments of pharmaceutical compositions for inhibiting leukocyte recruitment in a subject that comprise a therapeutically effective amount of at least one leukocyte recruitment inhibitor selected from compounds of formulae (I) and (II), enantiomers, diastereomers, racemates, tautomers, hydrates, solvates thereof, pharmaceutically acceptable salts, amides and esters thereof, further comprise a pharmaceutically acceptable carrier.

Embodiments of anti-inflammatory compositions that comprise a therapeutically effective amount of at least one anti-inflammatory compound selected from compounds of formulae (I) and (II), enantiomers, diastereomers, racemates, tautomers, hydrates, solvates thereof, pharmaceutically acceptable salts, amides and esters thereof, further comprise a pharmaceutically acceptable carrier.

Embodiments of methods for treating or preventing inflammation in a subject that comprise administering to the subject in connection with an inflammatory response a pharmaceutical composition comprising a therapeutically effective amount of at least one anti-inflammatory compound selected from compounds of formulae (I) and (II), enantiomers, diastereomers, racemates, tautomers, hydrates, solvates thereof, pharmaceutically acceptable salts, amides and esters thereof, include methods wherein said inflammatory response is a response to at least one of the conditions: inflammatory disorders, allergic disorders, dermatological disorders, autoimmune disease, lymphatic disorders, itchy skin, and immunodeficiency disorders.

Embodiments of methods for treating or preventing inflammation in a subject that comprise administering to the subject in connection with an inflammatory response a pharmaceutical composition comprising a therapeutically effective amount of at least one anti-inflammatory compound selected from compounds of formulae (I) and (II), enantiomers, diastereomers, racemates, tautomers, hydrates, solvates thereof, pharmaceutically acceptable salts, amides and esters thereof, include methods wherein said inflammatory response is a response to chemotherapy.

Embodiments of methods for treating or preventing inflammation in a subject that comprise administering to the subject in connection with an inflammatory response a pharmaceutical composition comprising a therapeutically effective amount of at least one anti-inflammatory compound selected from compounds of formulae (I) and (II), enantiomers, diastereomers, racemates, tautomers, hydrates, solvates thereof, pharmaceutically acceptable salts, amides and esters thereof, include methods wherein at least one of the following is satisfied: said inflammatory response is a response to a physical stimulus; said inflammatory response is a response to a chemical stimulus; said inflammatory response is a response to infection; said inflammatory response is a response to an invasion by a body that is foreign to said subject; said inflammatory response is a response to an immunological stimulus; said inflammatory response is a response to a non-immunological stimulus; said inflammatory response is a response to at least one of the conditions: Allergy, asthma, chronic obstructed pulmonary disease (COPD), atherosclerosis, rheumatoid arthritis, multiple sclerosis, inflammatory bowel disease, and more specifically wherein said inflammatory bowel disease is at least one of Crohn's disease and ulcerative colitis, psoriasis, allergic rhinitis, scleroderma, autoimmune thyroid disease, immune-mediated diabetes mellitus, and lupus; said inflammatory response is a response to at least one of the conditions: Myasthenia gravis, autoimmune neuropathy, and more specifically wherein said autoimmune neuropathy is Guillain-Barré neuropathy, autoimmune uveitis, autoimmune hemolytic anemia, pernicious anemia, autoimmune thrombocytopenia, temporal arteritis, anti-phospholipid syndrome, vasculitides, and more specifically wherein said vasculitides is Wegener's granulomatosis, Behcet's disease, dermatitis herpetiformis, pemphigus vulgaris, vitiligio, primary biliary cirrhosis, autoimmune hepatitis, autoimmune oophoritis, autoimmune orchitis, autoimmune disease of the adrenal gland, polymyositis, dermatomyositis, spondyloarthropathy, and more specifically wherein said spondyloarthropathy is ankylosing spondylitis, and Sjogren's syndrome; said inflammatory response is acute inflammation; said inflammatory response is allergic inflammation; and said inflammatory response is chronic inflammation. Administration in connection with an inflammatory response according to the present invention includes administration at a time that is at least one of prior to, at the onset of, and after inflammation is detected.

Embodiments of methods for modulating an $H_4$ receptor expression that comprise exposing an $H_4$ receptor to at least one compound selected from compounds of formulae (I) and (II), enantiomers, diastereomers, racemates, tautomers, hydrates, solvates thereof, pharmaceutically acceptable salts, amides and esters thereof, include methods wherein at least one of the following is satisfied: said at least one compound modulates the $H_4$ receptor expression as a receptor antagonist, and said at least one compound of modulates the $H_4$ receptor expression as a receptor partial agonist.

An illustration of the invention is a pharmaceutical composition made by mixing at least one imidazole compound selected from compounds of formulae (I) and (II), enantiomers, diastereomers, racemates, tautomers, hydrates, solvates thereof, pharmaceutically acceptable salts, amides and esters thereof, and a pharmaceutically acceptable carrier. Illustrating the invention is a process for making a pharmaceutical composition comprising mixing at least one imidazole compound selected from compounds of formulae (I) and (II), enantiomers, diastereomers, racemates, tautomers, hydrates, solvates thereof, pharmaceutically acceptable salts, amides and esters thereof, and a pharmaceutically acceptable carrier.

Another example of the invention is the use of a composition that comprises at least one imidazole compound selected from compounds of formulae (I) and (II), enantiomers, diastereomers, racemates, tautomers, hydrates, solvates thereof, pharmaceutically acceptable salts, amides and esters thereof, in the preparation of a medication for treating any one of the conditions referred to herein; one of such conditions is inflammation. Another example of the invention is the use of a composition that comprises at least one imidazole compound selected from compounds of formulae (I) and (II), enantiomers, diastereomers, racemates, tautomers, hydrates, solvates thereof, pharmaceutically acceptable salts, amides and esters thereof, in the treatment or prevention of any one of the conditions referred to herein; one of such conditions is inflammation.

The expression of the $H_4$ receptor in immune cells, including some leukocytes and mast cells, establishes it as an important target for therapeutic intervention in a range of immunological and inflammatory disorders (such as allergic, chronic, or acute inflammation). Specifically $H_4$ receptor ligands are expected to be useful for the treatment or prevention of various mammalian disease states.

Thus, according to the invention, the disclosed compounds, whether partial agonists or antagonists of the $H_4$ receptor, and compositions are useful for the amelioration of symptoms associated with, the treatment of, and the prevention of, the following conditions and diseases: inflammatory disorders, allergic disorders, dermatological disorders, autoimmune disease, lymphatic disorders, and immunodeficiency disorders, including the more specific conditions and diseases given above. The disclosed compounds may also be useful as adjuvants in chemotherapy or in the treatment of itchy skin.

Aspects of the invention include (a) a pharmaceutical composition comprising an imidazole compound selected from compounds of formulae (I) and (II), enantiomers, diastereomers, racemates, tautomers, hydrates, solvates thereof, pharmaceutically acceptable salts, amides and esters thereof, and a preferred compound as described herein, and a pharmaceutically acceptable carrier; (b) a packaged drug comprising (1) a pharmaceutical composition comprising at least one imidazole compound selected from compounds of formulae (I) and (II), enantiomers, diastereomers, racemates, tautomers, hydrates, solvates thereof, pharmaceutically acceptable salts, amides and esters thereof, or one or more preferred compounds as described herein, and a pharmaceutically acceptable carrier, and (2) instructions for the administration of said composition for the treatment or prevention of an $H_4$-mediated disease or condition.

Embodiments of this invention provide methods for treating an $H_4$-mediated condition in a patient, said methods comprising administering to the patient a pharmaceutically effective amount of a composition comprising at least one imidazole compound selected from compounds of formulae (I) and (II), enantiomers, diastereomers, racemates, tautomers, hydrates, solvates thereof, pharmaceutically acceptable salts, amides and esters thereof, and other disclosed or preferred compounds. In these conditions, the action of the $H_4$ receptor is involved. For example, the invention features a method for treating an $H_4$ mediated condition in a patient, said method comprising administering to the patient a pharmaceutically effective $H_4$-antagonizing amount of a composition comprising at least one imidazole compound selected from compounds of formulae (I) and (II), enantiomers, diastereomers, racemates, tautomers, hydrates, solvates thereof, pharmaceutically acceptable salts, amides and esters thereof.

The effect of an antagonist may also be produced by an inverse agonist. Inverse agonism describes the property of a compound to actively turn off a receptor that displays constitutive activity. Constitutive activity can be identified in cells that have been forced to over-express the human $H_4$ receptor. Constitutive activity can be measured by examining cAMP levels or by measuring a reporter gene sensitive to cAMP levels after a treatment with a cAMP-stimulating agent such as forskolin. Cells that over-express $H_4$ receptors will display lower cAMP levels after forskolin treatment than non-expressing cells. Compounds that behave as $H_4$ agonists will dose-dependently lower forskolin-stimulated cAMP levels in $H_4$-expressing cells. Compounds that behave as $H_4$ inverse agonists will dose-dependently stimulate cAMP levels in $H_4$-expressing cells. Compounds that behave as $H_4$ antagonists will block either $H_4$ agonist-induced inhibition of cAMP or $H_4$ inverse agonist-induced increases in cAMP.

Further embodiments of the invention include disclosed compounds that are inhibitors of a mammalian histamine $H_4$ receptor function, inhibitors of inflammation or inflammatory responses in vivo or in vitro, modulators of the expression of a mammalian histamine $H_4$ receptor protein, inhibitors of polymorphonuclear leukocyte activation in vivo or in vitro, or combinations of the above, and corresponding methods of treatment, prophylaxis, and diagnosis comprising the use of a disclosed compound.

The pharmaceutical compositions can be prepared using conventional pharmaceutical excipients and compounding techniques. Examples of suitable unit dosage forms are tablets, capsules, pills, powders, powder packets, granules, wafers, and the like, segregated multiples of any unit dosage form, as well as liquid solutions, and suspensions. Some liquid forms are aqueous, whereas other embodiments of liquid forms are non-aqueous. Oral dosage forms may be elixirs, syrups, capsules, tablets and the like. Examples of solid carriers include those materials usually employed in the manufacture of pills or tablets, such as lactose, starch, glucose, methylcellulose, magnesium stearate, dicalcium phosphate, mannitol and the like, thickeners such as tragacanth and methylcellulose USP, finely divided $SiO_2$, polyvinylpyrrolidone, magnesium stearate, and the like. Typical liquid oral excipients include ethanol, glycerol, water and the like. All excipients may be mixed as needed with diluents (for example, sodium and calcium carbonates, sodium and calcium phosphates, and lactose), disintegrants (for example, cornstarch and alginic acid), granulating agents, lubricants (for example, magnesium stearate, stearic acid, and talc), binders (for example, starch and gelatin), thickeners (for example, paraffin, waxes, and petrolatum), flavoring agents, coloring agents, preservatives, and the like by conventional techniques known to those of ordinary skill in the art of preparing dosage forms. Coatings can be present and include, for example, glyceryl monostearate and/or glyceryl diestearate. Capsules for oral use include hard gelatin capsules in which the active ingredient is mixed with a solid diluent, and soft gelatin capsules, in which the active ingredient is mixed with water or an oil, such as peanut oil, liquid paraffin, or olive oil.

Parenteral dosage forms may be prepared using water or another sterile carrier. Parenteral solutions can be packaged in containers adapted for subdivision into individual doses. For intramuscular, intraperitoneal, subcutaneous, and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone, and gum tragacanth, and a wetting agent, such as lecithin. Suitable preservatives for aqueous suspensions include ethyl and n-propyl p-hydroxybenzoate. Parenteral formulations include pharmaceutically acceptable aqueous or non-aqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbents, (h) lubricants, (i) buffering agents, and (j) propellants.

To aid solubility, suitable ingredients, such as cyclodextrins, may be included in the compositions. Appropriate cyclodextrins (CD) are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, for example randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD). The term mixed ether denotes cyclodextrin derivatives wherein at least two cyclodextrin hydroxy groups are etherified with different groups such as, for example, hydroxypropyl and hydroxyethyl.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

Physiologically acceptable carriers are well known in the art. Examples of liquid carriers are solutions in which compounds according to the present invention form solutions, emulsions, and dispersions. Compatible antioxidants, such as methylparaben and propylparaben, can be present in solid and/or liquid compositions, as can sweeteners.

Pharmaceutical compositions according to the present invention may include suitable emulsifiers typically used in emulsion compositions. Such emulsifiers are described in standard publications such as H. P. Fiedler, 1989, Lexikon der Hilfsstoffe für Pharmazie, Kosmetic und agrenzende Gebiete, Cantor ed., Aulendorf, Germany, and in Handbook of Pharmaceutical Excipients, 1986, American Pharmaceutical Association, Washington, D.C., and the Pharmaceutical Society of Great Britain, London, UK, which are incorporated herein by reference. Gelling agents may also be added to compositions according to this invention. Polyacrylic acid derivatives, such as carbomers, are examples of gelling agents, and more particularly, various types of carbopol, which are typically used in amounts from about 0.2% to about 2%. Suspensions may be prepared as a cream, an ointment, including a water-free ointment, a water-in-oil emulsion, an oil-in-water emulsion, an emulsion gel, or a gel.

It is anticipated that the compounds of the invention can be administered by oral or parenteral routes, including intravenous, intramuscular, intraperitoneal, subcutaneous, rectal, intracisternal, intravaginal, intravesical, topical or local administration, and by inhalation (bucal or nasal, preferably in the form of a spray). For oral administration, the compounds of the invention will generally be provided in the form of tablets, capsules, or as a solution or suspension. Other methods of administration include controlled release formulations, such as subcutaneous implants and dermal patches.

Compounds according to the present invention and mixtures thereof provide embodiments of active substance in pharmaceutical compositions that can be made with excipients and ingredients and with ordinary skill in the art. Lists of excipients and ingredients for pharmaceutical compositions are available in standard references. For example, a standard text such as The Science and Practice of Pharmacy; A. R. Gennaro, ed., provides 20 chapters in part 5, pp. 669-1050, on pharmaceutical manufacturing, including lists of ingredients to manufacture pharmaceutical compositions such as solutions (including aromatic waters, aqueous acids, douches, enemas, gargles, mouthwashes, juices, nasal solutions, otic solutions, irrigation solutions, syrups, honeys, mucilages, jellies, collodions, elixirs, glycerins, inhalants, liniments, oleopreparations, spirits, and drops), emulsions (including multiple emulsions and microemulsions), suspensions, (including gels, lotions, tablet-formulated suspensions, magmas and milks, mixtures, and official suspensions), extracts, parenteral preparations, intravenous preparations, ophthalmic preparations, topical preparations, oral solid dosage forms, coatings, controlled-release drug delivery systems, aerosols, packaging materials, antioxidants, preservatives, coloring agents, flavoring agents, diluting agents, vehicles, emulsifying agents, suspending agents, ointment bases, pharmaceutical solvents, and miscellaneous pharmaceutical necessities, including the techniques and devices for manufacturing such preparations.

Effective doses of the compounds of the present invention may be ascertained by conventional methods. The specific dosage level required for any particular patient will depend on a number of factors, including severity of the condition, type of symptoms needing treatment, the route of administration, the weight, age, and general condition of the patient, and the administration of other medicaments. In general, it is anticipated that the daily dose (whether administered as a single dose or as divided doses) will be in the range from about 0.01 mg to about 1000 mg per day, more usually from about 1 mg to about 500 mg per day, and most usually form about 10 mg to about 200 mg per day. Expressed as dosage per unit body weight, a typical dose will be expected to be between about 0.0001 mg/kg and about 15 mg/kg, especially between about 0.01 mg/kg and about 7 mg/kg, and most especially between about 0.15 mg/kg and 2.5 mg/kg.

Anticipated oral dose ranges include from about 0.01 to 500 mg/kg, daily, more preferably from about 0.05 to about 100 mg/kg, taken in 14 separate doses. Some compounds of the invention may be orally dosed in the range of about 0.05 to about 50 mg/kg daily, while others may be dosed at 0.05 to about 20 mg/kg daily. Infusion doses can range from about 1.0 to about $1.0 \times 10^4$ μg/(kg min) of inhibitor, admixed with a pharmaceutical carrier over a period ranging from several minutes to several days. For topical administration, compounds of the present invention may be mixed with a pharmaceutical carrier at a concentration from about 0.1 to about 10% of drug to vehicle. Capsules, tablets or other formulations (such as liquids and film-coated tablets) may be of between 0.5 and 200 mg, such as 1, 3, 5, 10, 15, 25, 35, 50 mg, 60 mg, and 100 mg and can be administered according to the disclosed methods. Daily dosages are envisaged to be, for example, between 10 mg and 5000 mg for an adult human being of normal weight.

EXAMPLES

General Experimental Methods

Nuclear magnetic resonance (NMR) spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Mass spectra (MS) were obtained on a Hewlett Packard (Agilent) series 1100 MSD using electrospray ionization (ESI) in either positive or negative mode as indicated. The "mass calculated" (calcd) for a molecular formula is the monoisotopic mass of the compound.

Purification Method 1:

2-Arylimidazoles were purified by chromatography (silica gel, 0-10% (2.0 M ammonia in methanol) in dichloromethane. The reaction mixtures were loaded on silica gel without work-up.

Example 1

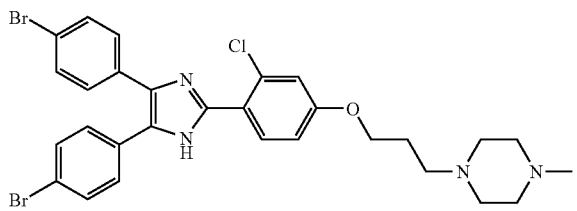

1-(3-{4-[4,5-Bis-(4-bromo-phenyl)-1H-imidazol-2-yl]-3-chloro-phenoxy}-propyl)-4-methyl-piperazine General Procedure 1.

A. 2-Chloro-4-(3-chloro-propoxy)-benzaldehyde. 1-Bromo-3-chloropropane (2.55 g, 16.2 mmol, 1.0 equiv) was added to a solution of 2-chloro-4-hydroxybenzaldehyde (2.54 g, 16.2 mmol) and $K_2CO_3$ (4.48 g, 32.4 mmol) in acetonitrile (41 mL). The mixture was heated at 65° C. for 18 h, then cooled to room temperature (rt) and filtered through diatomaceous earth. The filtrate was concentrated to yield the crude product, which was purified by column chromatography (silica gel, 5% EtOAc in hexanes) to afford 3.19 g of a colorless oil (66%). $^1$H NMR (400 MHz, $CD_3OD$): 10.3 (s, 1H), 7.87 (d, J=8.0, 1H), 7.10 (d, J=4.0, 1H), 7.03 (dd, J=8.0, 4.0, 1H), 4.23 (t, J=8.0, 2H), 3.76 (t, J=8.0, 2H), 2.31-2.22 (m, 2H).

General Procedure 2.

B. 2-Chloro-4-[3-(4-methyl-piperazin-1-yl)-propoxy]-benzaldehyde. N-Methylpiperazine (2.16 g, 21.5 mmol), 2-chloro-4-(3-chloro-propoxy)-benzaldehyde (3.19 g, 10.8 mmol), $K_2CO_3$ (4.46 g, 32.3 mmol), and KI (1.02 g, 5.38 mmol) were stirred in n-butanol (22 mL) at 90° C. for 18 h. The reaction mixture was diluted with water and then extracted three times with EtOAc. The combined extracts were dried ($Na_2SO_4$), filtered, and concentrated, yielding the crude product, which was purified by Method 1 to afford 2.04 g (63%) of an orange oil. $^1$H NMR (400 MHz, $CD_3OD$): 10.3 (s, 1H), 7.86 (d, J=8.0, 1H), 7.08 (d, J=2.0, 1H), 7.00 (dd, J=8.0, 2.0, 1H), 4.15 (t, J=8.0, 2H), 3.00-2.30 (br s, 10H), 2.29 (s, 3H), 2.05-1.90 (m, 2H).

General Procedure 3.

C. 1-(3-{4-[4,5-Bis-(4-bromo-phenyl)-1H-imidazol-2-yl]-3-chloro-phenoxy}-propyl)-4-methyl-piperazine. 2-Chloro-4-[3-(4-methyl-piperazin-1-yl)-propoxy]-benzaldehyde (37 mg, 0.12 mmol) and 1,2-bis-(4-bromo-phenyl)-ethane-1,2-dione (59 mg, 0.16 mmol) were stirred with $NH_4OAc$ (28 mg, 0.37 mmol) in methanol (0.25 M) at 65° C. for 2 d. The reaction mixture was purified by Method 1 to afford 22 mg (28%) of the title compound. MS (ESI): mass calcd for $C_{29}H_{29}Br_2ClN_4O$, 642.04; m/z found, 645.0 $[M+H]^+$. $^1$H NMR (400 MHz, $CD_3OD$): 7.62 (d, J=8.6, 1H), 7.50 (d, J=8.0, 4H), 7.38 (d, J=7.9, 4H), 7.12 (d, J=2.5, 1H), 7.00 (dd, J=8.7, 2.5, 1H), 4.10 (t, J=6.1, 2H), 2.85-2.25 (m, 10H), 2.29 (s, 3H), 2.02-1.98 (m, 2H).

The following compounds in Examples 2-13 were prepared using methods analogous to those described in Example 1 with the appropriate substituent changes.

Example 2

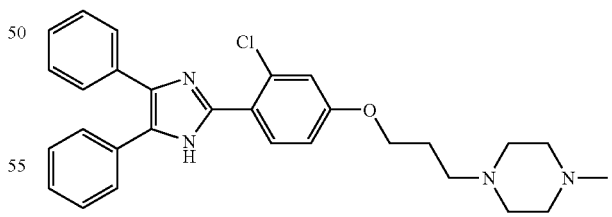

1-{3-[3-Chloro-4-(4,5-diphenyl-1H-imidazol-2-yl)-phenoxy]-propyl}-4-methyl-piperazine MS (ESI): mass calcd for $C_{29}H_{31}ClN_4O$, 486.22; m/z found, 487.5 $[M+H]^+$. $^1$H NMR (400 MHz, $CD_3OD$): 7.64 (d, J=8.6, 1H), 7.49-7.46 (m, 4H), 7.35-7.25 (m, 6H), 7.12 (d, J=2.5, 1H), 7.00 (dd, J=8.7, 2.5, 1H), 4.09 (t, J=6.1, 2H), 2.80-2.35 (m, 10H), 2.29 (s, 3H), 2.02-1.98 (m, 2H).

Example 3

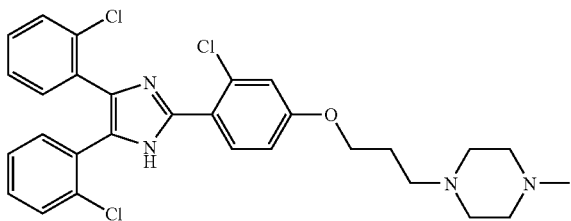

1-(3-{4-[4,5-Bis-(2-chloro-phenyl)-1H-imidazol-2-yl]-3-chloro-phenoxy}-propyl)-4-methyl-piperazine MS (ESI): mass calcd for $C_{29}H_{29}Cl_3N_4O$, 554.14; m/z found, 557.5 [M+H]+. $^1$H NMR (400 MHz, CD$_3$OD): 7.69 (d, J=8.7, 1H), 7.42-7.20 (m, 8H), 7.12 (d, J=2.5, 1H), 7.00 (dd, J=8.7, 2.5, 1H), 4.09 (t, J=6.1, 2H), 2.80-2.35 (m, 10H), 2.29 (s, 3H), 2.02-1.98 (m, 2H).

Example 4

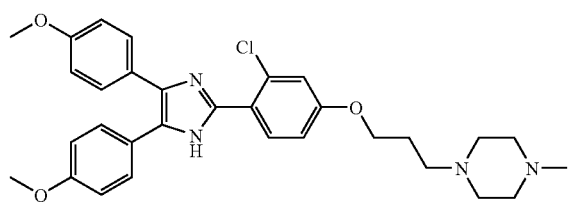

1-(3-{4-[4,5-Bis-(4-methoxy-phenyl)-1H-imidazol-2-yl]-3-chloro-phenoxy}-propyl)-4-methyl-piperazine MS (ESI): mass calcd for $C_{31}H_{35}ClN_4O_3$, 546.24; m/z found, 547.5 [M+H]+. $^1$H NMR (400 MHz, CD$_3$OD): 7.61 (d, J=8.6, 1H), 7.38 (d, J=8.8, 4H), 7.10 (d, J=2.5, 1H), 6.97 (dd, J=8.6, 2.5, 1H), 6.88 (d, J=8.8, 4H), 4.08 (t, J=6.1, 2H), 3.79 (s, 6H), 2.80-2.35 (m, 10H), 2.29 (s, 3H), 2.05-1.95 (m, 2H).

Example 5

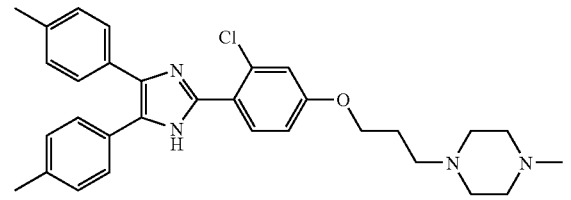

1-{3-[3-Chloro-4-(4,5-di-p-tolyl-1H-imidazol-2-yl)-phenoxy]-propyl}-4-methyl-piperazine MS (ESI): mass calcd for $C_{31}H_{35}ClN_4O$, 514.25; m/z found, 515.2 [M+H]+. $^1$H NMR (400 MHz, CD$_3$OD): 7.62 (d, J=8.6, 1H), 7.35 (d, J=7.8, 4H), 7.13 (d, J=7.9, 4H), 7.10 (d, J=2.5, 1H), 6.98 (dd, J=8.6, 2.5, 1H), 4.08 (t, J=6.1, 2H), 2.80-2.35 (m, 10H), 2.33 (s, 6H), 2.28 (s, 3H), 2.01-1.96 (m, 2H).

Example 6

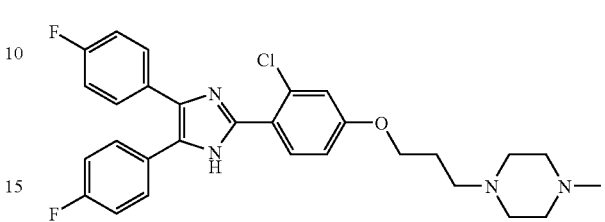

1-(3-{4-[4,5-Bis-(4-fluoro-phenyl)-1H-imidazol-2-yl]-3-chloro-phenoxy}-propyl)-4-methyl-piperazine MS (ESI): mass calcd for $C_{29}H_{29}ClF_2N_4O$, 522.20; m/z found, 523.2 [M+H]+. $^1$H NMR (400 MHz, CD$_3$OD): 7.63 (d, J=8.6, 1H), 7.48-7.44 (m, 4H), 7.12 (d, J=2.5, 1H), 7.11-7.06 (m, 4H), 7.00 (dd, J=8.7, 2.5, 1H), 4.10 (t, J=6.1, 2H), 2.80-2.35 (m, 10H), 2.30 (s, 3H), 2.03-1.98 (m, 2H).

Example 7

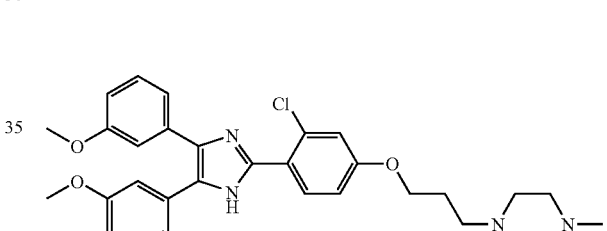

1-(3-{4-[4,5-Bis-(3-methoxy-phenyl)-1H-imidazol-2-yl]-3-chloro-phenoxy}-propyl)-4-methyl-piperazine MS (ESI): mass calcd for $C_{31}H_{35}ClN_4O_3$, 546.24; m/z found, 547.2 [M+H]+. $^1$H NMR (400 MHz, CD$_3$OD): 7.63 (d, J=8.6, 1H), 7.27-7.22 (m, 2H), 7.12 (d, J=2.5, 1H), 7.09-7.05 (m, 4H), 7.00 (dd, J=8.7, 2.5, 1H), 6.86-6.84 (m, 2H), 4.09 (t, J=6.1, 2H), 3.72 (s, 6H), 2.80-2.35 (m, 10H), 2.29 (s, 3H), 2.05-1.95 (m, 2H).

Example 8

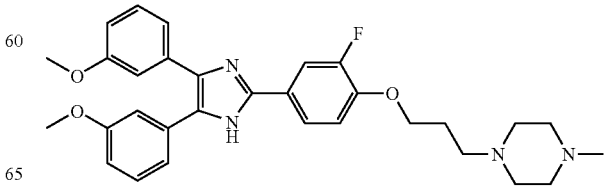

1-(3-{4-[4,5-Bis-(3-methoxy-phenyl)-1H-imidazol-2-yl]-2-fluoro-phenoxy}-propyl)-4-methyl-piperazine MS (ESI): mass calcd for C$_{31}$H$_{35}$FN$_4$O$_3$, 530.27; m/z found, 531.2 [M+H]$^+$. $^1$H NMR (400 MHz, CD$_3$OD): 7.78-7.71 (m, 2H), 7.28-7.24 (m, 2H), 7.17-7.06 (m, 5H), 6.89-6.86 (m, 2H), 4.12 (t, J=6.1, 2H), 3.74 (s, 6H), 2.80-2.35 (m, 10H), 2.29 (s, 3H), 2.03-1.99 (m, 2H).

Example 9

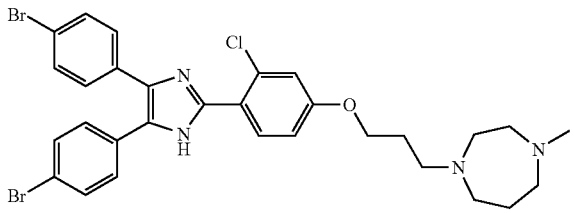

1-(3-{4-[4,5-Bis-(4-bromo-phenyl)-1H-imidazol-2-yl]-3-chloro-phenoxy}-propyl)-4-methyl-[1,4]diazepane MS (ESI): mass calcd for C$_{30}$H$_{31}$Br$_2$ClN$_4$O, 656.06; m/z found, 659.0 [M+H]$^+$. $^1$H NMR (400 MHz, CD$_3$OD): 7.52 (d, J=8.6, 1H), 7.40 (d, J=7.6, 4H), 7.28 (d, J=8.6, 4H), 7.02 (d, J=2.5, 1H), 6.90 (dd, J=8.6, 4.0, 1H), 4.01 (d, J=5.0, 2H), 2.71-2.64 (m, 4H), 2.62-2.55 (m, 6H), 2.25 (s, 3H), 1.92-1.81 (m, 2H), 1.78-1.69 (m, 2H).

Example 10

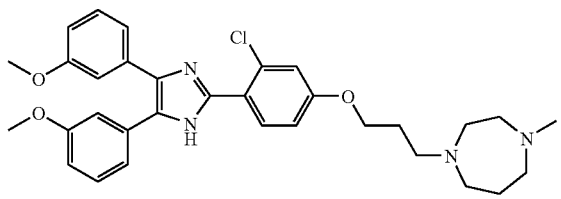

1-(3-{4-[4,5-Bis-(3-methoxy-phenyl)-1H-imidazol-2-yl]-3-chloro-phenoxy}-propyl)-4-methyl-[1,4]diazepane MS (ESI): mass calcd for C$_{32}$H$_{37}$ClN$_4$O$_3$, 560.26; m/z found, 561.2 [M+H]$^+$. $^1$H NMR (400 MHz, CD$_3$OD): 7.66 (d, J=8.6, 1H), 7.30-7.23 (m, 2H), 7.14 (d, J=2.5, 1H), 7.11-7.08 (m, 4H), 7.02 (dd, J=8.6, 2.5, 1H), 6.90-6.85 (m, 2H), 4.12 (t, J=6.3, 2H), 3.75 (s, 6H), 2.83-2.78 (m, 4H), 2.75-2.68 (m, 6H), 2.37 (s, 3H), 2.04-1.95 (m, 2H), 1.90-1.83 (m, 2H).

Example 11

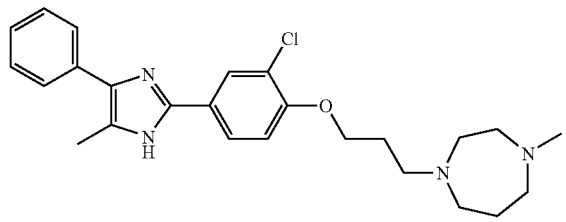

1-{3-[2-Chloro-4-(5-methyl-4-phenyl-1H-imidazol-2-yl)-phenoxy]-propyl}-4-methyl-[1,4]diazepane MS (ESI): mass calcd for C$_{25}$H$_{31}$ClN$_4$O, 438.22; m/z found, 439.5 [M+H]$^+$. $^1$H NMR (400 MHz, CD$_3$OD): 7.94 (d, J=2.2, 1H), 7.77 (dd, J=8.6, 2.2, 1H), 7.60-7.55 (m, 2H), 7.43-7.39 (m, 2H), 7.29-7.25 (m, 1H), 7.09 (d, J=8.7, 1H), 4.11 (t, J=6.0, 2H), 2.78-2.65 (m, 10H), 2.41 (s, 3H), 2.32 (s, 3H), 2.01-1.93 (m, 2H), 1.85-1.79 (m, 2H).

Example 12

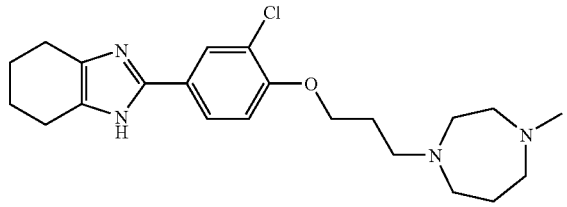

2-{3-Chloro-4-[3-(4-methyl-[1,4]diazepan-1-yl)-propoxy]-phenyl}-4,5,6,7-tetrahydro-1H-benzoimidazole MS (ESI): mass calcd for C$_{22}$H$_{31}$ClN$_4$O, 402.22; m/z found, 403.4 [M+H]$^+$. $^1$H NMR (400 MHz, CD$_3$OD): 7.82 (d, J=2.2, 1H), 7.67 (dd, J=8.6, 2.2, 1H); 7.09 (d, J=8.7, 1H), 4.13 (t, J=6.0, 2H), 2.80-2.56 (m, 14H), 2.34 (s, 3H), 2.03-1.96 (m, 2H), 1.86-1.80 (m, 6H).

Example 13

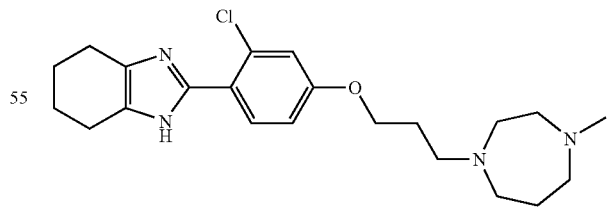

2-{2-Chloro-4-[3-(4-methyl-[1,4]diazepan-1-yl)-propoxy]-phenyl}-4,5,6,7-tetrahydro-1H-benzoimidazole MS (ESI): mass calcd for C$_{22}$H$_{31}$ClN$_4$O, 402.22; m/z found, 403.2 [M+H]$^+$. $^1$H NMR (400 MHz, CD$_3$OD): 7.47 (d, J=8.7, 1H), 6.93 (d, J=2.5, 1H), 6.83 (dd, J=8.7, 2.5, 1H), 3.95 (t, J=6.1, 2H), 2.70-2.47 (m, 14H), 2.25 (s, 3H), 1.87-1.80 (m, 2H), 1.74-1.70 (m, 6H).

Example 14

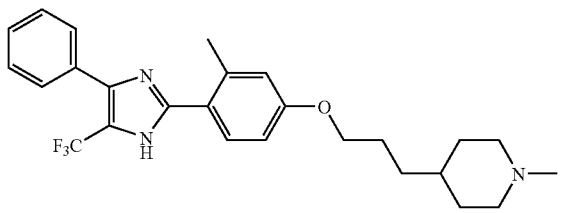

1-Methyl-4-{3-[3-methyl-4-(4-phenyl-5-trifluoromethyl-1H-imidazol-2-yl)-phenoxy]-propyl}-piperidine A. 3-(1-Methyl-piperidin-4-yl)-propan-1-ol. To a refluxing solution of 1 M LiAlH$_4$ (40 mmol) in THF (30 mL) was added dropwise a solution of N—BOC-4-piperidinepropionic acid (3.0 g, 11.6 mmol). The reaction mixture was heated for 3 h then cooled to rt. Upon further cooling to 0° C., water (1.5 mL) was added slowly, and the reaction mixture was allowed to warm to rt over 15 min. The mixture was again cooled to 0° C., and 10% aq. NaOH (1.5 mL) was added slowly. Upon warming to rt over 15 min, the mixture was cooled to 0° C. and more water (4.5 mL) was added. The resultant mixture was allowed to warm to rt over 18 h, and was then filtered through a pad of diatomaceous earth. The filtrate was concentrated, and the residue was purified by Method 1 to afford 1.9 g (100%) of 3-(1-methyl-piperidin-4-yl)-propan-1-ol as a yellow oil. MS (ESI): mass calcd for C$_9$H$_{19}$NO, 157.15; m/z found 158.1 [M+H]$^+$. $^1$H NMR (400 MHz, CD$_3$OD): 3.45-3.41 (m, 2H), 2.77-2.74 (m, 2H), 1.89-1.85 (m, 2H), 1.64-1.61 (m, 2H), 1.47-1.43 (m, 2H), 1.21-1.12 (m, 5H).

General Procedure 4.

B. 4-[3-(1-Methyl-piperidin-4-yl)-propoxy]-benzaldehyde. To an ice-cooled solution of 2-methyl-4-hydroxybenzaldehyde (722 mg, 5.3 mmol), PPh$_3$ polymer resin (3 mmol/g, 2.2 g, 6.4 mmol), and 3-(1-methyl-piperidin-4-yl)-propan-1-ol (833 mg, 5.3 mmol, 1.0 equiv) in THF (25 mL) was added di-tert-butyl-azodicarboxylate (1.47 g, 6.4 mmol). The reaction mixture was allowed to warm to rt and was stirred for 16 h. The mixture was filtered through diatomaceous earth, diluted with water, and extracted three times with EtOAc. The combined extracts were dried (Na$_2$SO$_4$) and concentrated. Purification by Method 1 afforded 578 mg (40%) of the desired aldehyde. MS (ESI): mass calcd for C$_{16}$H$_{23}$NO$_2$, 261.17; m/z found, 262.2 [M+H]$^+$. $^1$H NMR (400 MHz, CDCl$_3$): 9.85 (s, 1H), 7.80 (d, J=8.6, 2H), 6.97 (d, J=8.6, 2H), 4.01 (t, J=6.4, 2H), 2.84-2.82 (m, 2H), 2.25 (s, 3H), 1.92-1.78 (m, 4H), 1.71-1.69 (m, 2H), 1.41-1.37 (m, 2H), 1.29-1.26 (m, 3H).

C. 1-Methyl-4-{3-[3-methyl-4-(4-phenyl-5-trifluoromethyl-1H-imidazol-2-yl)-phenoxy]-propyl}-piperidine. The title compound (27 mg, 21%) was prepared as described in General Procedure 3 with the appropriate substituent changes. MS (ESI): mass calcd for C$_{26}$H$_{30}$F$_3$N$_3$O, 457.23; m/z found, 458.4 [M+H]$^+$. $^1$H NMR (400 MHz, CD$_3$OD): 7.60-7.53 (m, 2H), 7.54-7.44 (m, 4H), 6.91 (d, J=2.3, 1H), 6.87 (dd, J=8.5, 2.5, 1H), 4.04 (t, J=6.4, 2H), 2.92-2.89 (m, 2H), 2.47 (s, 3H), 2.28 (s, 3H), 2.04-2.00 (m, 2H), 1.86-1.77 (m, 4H), 1.51-1.28 (m, 5H).

The following compounds in Examples 15-25 were prepared using procedures analogous to those described in Example 14 with the appropriate substituent changes.

Example 15

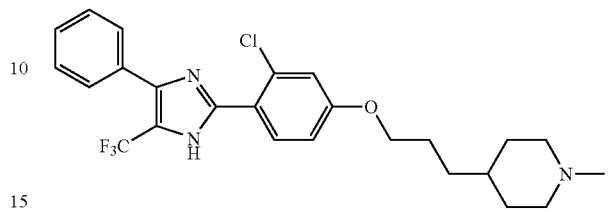

4-{3-[3-Chloro-4-(4-phenyl-5-trifluoromethyl-1H-imidazol-2-yl)-phenoxy]-propyl}-1-methyl-piperidine MS (ESI): mass calcd for C$_{25}$H$_{27}$ClF$_3$N$_3$O, 477.18; m/z found, 478.3 [M+H]$^+$. $^1$H NMR (400 MHz, CD$_3$OD): 7.63-7.56 (m, 3H), 7.54-7.44 (m, 3H), 7.13 (d, J=2.5, 1H), 7.01 (dd, J=8.7, 2.5, 1H), 4.05 (t, J=6.4, 2H), 2.92-2.85 (m, 2H), 2.28 (s, 3H), 2.07-1.98 (m, 2H), 1.88-1.71 (m, 4H), 1.51-1.41 (m, 2H), 1.40-1.22 (m, 3H).

Example 16

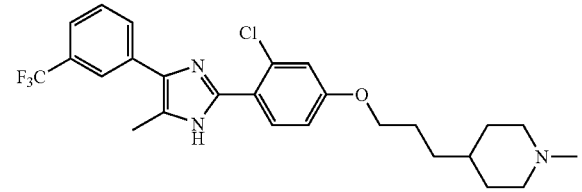

4-(3-{3-Chloro-4-[5-methyl-4-(3-trifluoromethyl-phenyl)-1H-imidazol-2-yl]-phenoxy}-propyl)-1-methyl-piperidine MS (ESI): mass calcd for C$_{26}$H$_{29}$ClF$_3$N$_3$O, 491.20; m/z found, 492.4 [M+H]$^+$. $^1$H NMR (400 MHz, CD$_3$OD): 7.97-7.87 (m, 2H), 7.66-7.54 (m, 3H), 7.10 (d, J=2.5, 1H), 6.99 (dd, J=8.8, 2.5, 1H), 4.05 (t, J=6.4, 2H), 2.92-2.85 (m, 2H), 2.50 (s, 3H), 2.28 (s, 3H), 2.08-1.95 (m, 2H), 1.88-1.70 (m, 4H), 1.59-1.21 (m, 5H).

Example 17

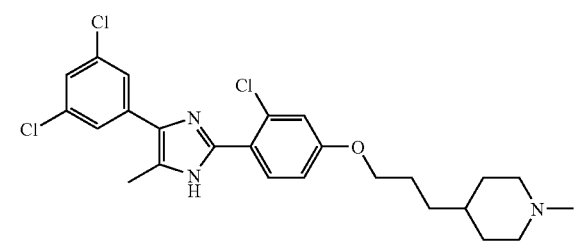

4-(3-{3-Chloro-4-[4-(3,5-dichloro-phenyl)-5-methyl-1H-imidazol-2-yl]-phenoxy}-propyl)-1-methyl-piperidine MS (ESI): mass calcd for $C_{25}H_{28}Cl_3N_3O$, 491.13; m/z found, 492.3 [M+H]$^+$. $^1$H NMR (400 MHz, CD$_3$OD): 7.61-7.54 (m, 3H), 7.32-7.30 (m, 1H), 7.07 (d, J=2.5, 1H), 6.96 (dd, J=8.7, 2.5, 1H), 4.03 (t, J=6.4, 2H), 2.91-2.82 (m, 2H), 2.47 (s, 3H), 2.26 (s, 3H), 2.06-1.95 (m, 2H), 1.86-1.66 (m, 4H), 1.57-1.17 (m, 5H).

Example 18

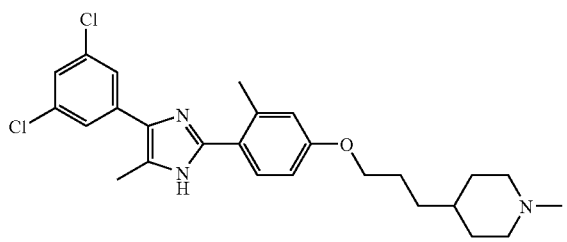

4-(3-{4-[4-(3,5-Dichloro-phenyl)-5-methyl-1H-imidazol-2-yl]-3-methyl-phenoxy}-propyl)-1-methyl-piperidine MS (ESI): mass calcd for $C_{26}H_{31}Cl_2N_3O$, 471.18; m/z found, 472.3 [M+H]$^+$. $^1$H NMR (400 MHz, CD$_3$OD): 7.59-7.55 (m, 2H), 7.37 (d, J=8.3, 1H), 7.30-7.27 (m, 1H), 7.84 (d, J=2.5, 1H), 6.81 (dd, J=8.6, 2.5, 1H), 3.99 (t, J=6.3, 2H), 2.91-2.83 (m, 2H), 2.46 (s, 3H), 2.44 (s, 3H), 2.26 (s, 3H), 2.07-1.97 (m, 2H), 1.84-1.72 (m, 4H), 1.46-1.19 (m, 5H).

Example 19

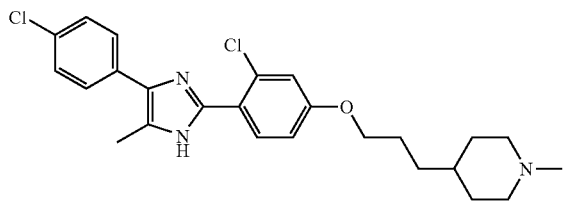

4-(3-{3-Chloro-4-[4-(4-chloro-phenyl)-5-methyl-1H-imidazol-2-yl]-phenoxy}-propyl)-1-methyl-piperidine MS (ESI): mass calcd for $C_{25}H_{29}Cl_2N_3O$, 457.17; m/z found, 458.3 [M+H]$^+$. $^1$H NMR (400 MHz, CD$_3$OD): 7.61-7.54 (m, 3H), 7.42-7.37 (m, 2H), 7.06 (d, J=2.5, 1H), 6.95 (dd, J=8.6, 2.3, 1H), 4.01 (t, J=6.3, 2H), 2.90-2.81 (m, 2H), 2.43 (s, 3H), 2.25 (s, 3H), 2.05-1.94 (m, 2H), 1.85-1.69 (m, 4H), 1.46-1.19 (m, 5H).

Example 20

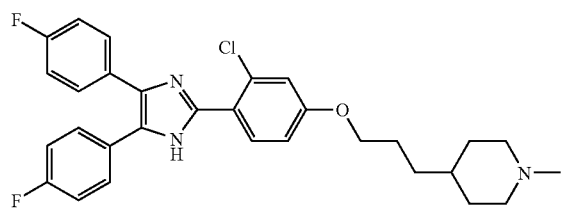

4-(3-{4-[4,5-Bis-(4-fluoro-phenyl)-1H-imidazol-2-yl]-3-chloro-phenoxy}-propyl)-1-methyl-piperidine MS (ESI): mass calcd for $C_{30}H_{30}ClF_2N_3O$, 521.20; m/z found, 522.2 [M+H]$^+$. $^1$H NMR (400 MHz, CD$_3$OD): 7.63 (d, J=8.6, 1H), 7.50-7.42 (m, 4H), 7.12-7.04 (m, 5H), 6.99 (dd, J=8.6, 2.5, 1H), 4.04 (t, J=6.1, 2H), 2.91-2.83 (m, 2H), 2.26 (s, 3H), 2.06-1.95 (m, 2H), 1.87-1.71 (m, 4H), 1.48-1.16 (m, 5H).

Example 21

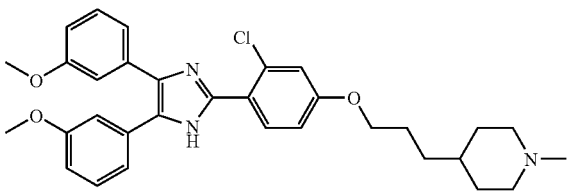

4-(3-{4-[4,5-Bis-(3-methoxy-phenyl)-1H-imidazol-2-yl]-3-chloro-phenoxy}-propyl)-1-methyl-piperidine MS (ESI): mass calcd for $C_{32}H_{36}ClN_3O_3$, 545.24; m/z found, 546.2 [M+H]$^+$. $^1$H NMR (400 MHz, CD$_3$OD): 7.62 (d, J=8.6, 1H), 7.27-7.19 (m, 2H), 7.10-7.01 (m, 5H), 6.97 (dd, J=8.3, 2.5, 1H), 6.87-6.81 (m, 2H), 4.02 (t, J=6.3, 2H), 3.71 (s, 6H), 2.90-2.81 (m, 2H), 2.25 (s, 3H), 2.05-1.94 (m, 2H), 1.84-1.70 (m, 4H), 1.47-1.15 (m, 5H).

Example 22

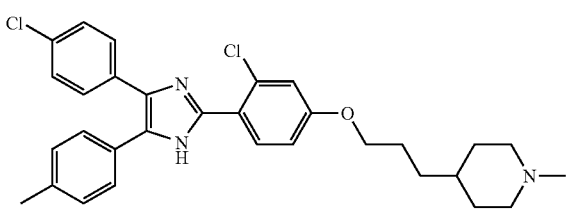

4-(3-{3-Chloro-4-[4-(4-chloro-phenyl)-5-p-tolyl-1H-imidazol-2-yl]-phenoxy}-propyl)-1-methyl-piperidine MS (ESI): mass calcd for $C_{31}H_{33}Cl_2N_3O$, 533.20; m/z found, 534.4 [M+H]$^+$. $^1$H NMR (400 MHz, CD$_3$OD): 7.62 (d, J=8.6, 1H), 7.49-7.41 (m, 2H), 7.36-7.28 (m, 4H), 7.20-7.15 (m, 2H), 7.09 (d, J=2.5, 1H), 6.98 (dd, J=8.6, 2.5, 1H), 4.03 (t, J=6.3, 2H), 2.91-2.83 (m, 2H), 2.35 (s, 3H), 2.27 (s, 3H), 2.07-1.97 (m, 2H), 1.86-1.70 (m, 4H), 1.47-1.19 (m, 5H).

Example 23

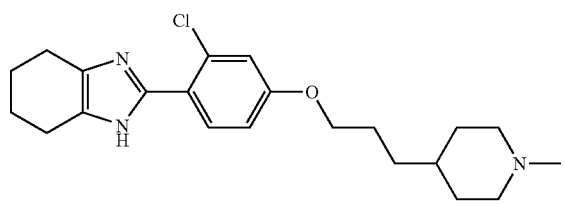

2-{2-Chloro-4-[3-(1-methyl-piperidin-4-yl)-propoxy]-phenyl}-4,5,6,7-tetrahydro-1H-benzoimidazole MS (ESI): mass calcd for $C_{22}H_{30}ClN_3O$, 387.21; m/z found, 388.3 [M+H]$^+$. $^1$H NMR (400 MHz, CD$_3$OD): 7.56 (d, J=8.6, 1H), 7.02 (d, J=2.5, 1H), 6.92 (dd, J=8.8, 2.5, 1H), 4.01 (t, J=6.3, 2H), 2.95-2.85 (m, 2H), 2.64-2.56 (m, 2H), 2.29 (s, 3H), 2.13-2.00 (m, 2H), 1.87-1.00 (m, 15H).

Example 24

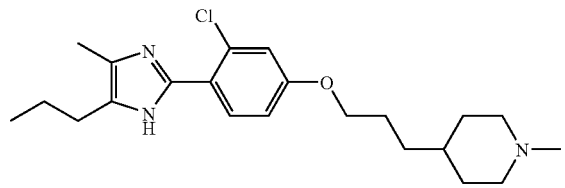

4-{3-[3-Chloro-4-(4-methyl-5-propyl-1H-imidazol-2-yl)-phenoxy]-propyl}-1-methyl-piperidine MS (ESI): mass calcd for $C_{22}H_{32}ClN_3O$, 389.22; m/z found, 390.4 [M+H]$^+$. $^1$H NMR (400 MHz, CD$_3$OD): 7.51 (d, J=8.6, 1H), 7.02 (d, J=2.8, 1H), 6.92 (dd, J=9.1, 2.8, 1H), 4.00 (t, J=6.6, 2H), 2.91-2.84 (m, 2H), 2.53 (t, J=7.6, 2H), 2.26 (s, 3H), 2.18 (s, 3H), 2.05-1.96 (m, 2H), 1.84-1.71 (m, 4H), 1.67-1.57 (m, 2H), 1.49-1.19 (m, 5H), 0.94 (t, J=7.3, 3H).

Example 25

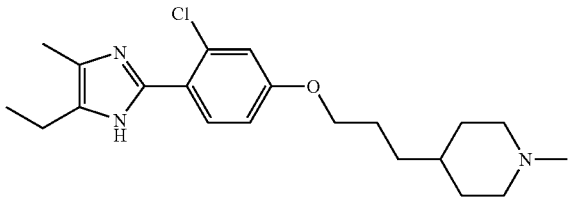

4-{3-[3-Chloro-4-(5-ethyl-4-methyl-1H-imidazol-2-yl)-phenoxy]-propyl}-1-methylpiperidine MS (ESI): mass calcd for $C_{21}H_{30}ClN_3O$, 375.21; m/z found, 376.4 [M+H]$^+$. $^1$H NMR (400 MHz, CD$_3$OD): 7.52 (d, J=8.8, 1H), 7.02 (d, J=2.5, 1H), 6.91 (dd, J=8.6, 2.5, 1H), 4.00 (t, J=6.6, 2H), 2.95-2.88 (m, 2H), 2.57 (q, J=7.6, 2H), 2.31 (s, 3H), 2.18 (s, 3H), 2.14-2.04 (m, 2H), 1.85-1.73 (m, 4H), 1.47-1.23 (m, 5H), 1.20 (t, J=7.6, 3H).

Example 26

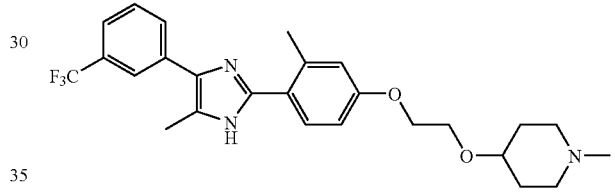

1-Methyl-4-(2-{3-methyl-4-[5-methyl-4-(3-trifluoromethyl-phenyl)-1H-imidazol-2-yl]-phenoxy}-ethoxy)-piperidine This compound was prepared from 2-methyl-4-[2-(1-methyl-piperidin-4-yloxy)-ethoxy]-benzaldehyde, using methods similar to those described in General Procedure 3. MS (ESI): mass calcd for $C_{26}H_{30}F_3N_3O_2$, 473.23; m/z found, 474.4 [M+H]$^+$. $^1$H NMR (400 MHz, CD$_3$OD): 7.93-7.83 (m, 2H), 7.63-7.51 (m, 2H), 7.41 (d, J=7.4, 1H), 6.90-6.80 (m, 1H), 6.85 (dd, J=8.3, 2.5, 1H), 4.16-4.11 (m, 2H), 3.85-3.79 (m, 2H), 3.54-3.44 (m, 1H), 2.78-2.64 (m, 2H), 2.47 (s, 3H), 2.46 (s, 3H), 2.30-2.16 (m, 5H), 1.99-1.88 (m, 2H), 1.72-1.59 (m, 2H).

Example 27

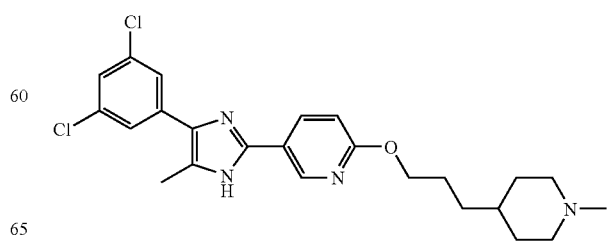

5-[4-(3,5-Dichloro-phenyl)-5-methyl-1H-imidazol-2-yl]-2-[3-(1-methyl-piperidin-4-yl)-propoxy]-pyridine General Procedure 5.

A. 6-[3-(1-Methyl-piperidin-4-yl)-propoxy]-nicotinonitrile. To a stirred solution of 3-(1-methyl-piperidin-4-yl)-propan-1-ol (5.0 g, 31.7 mmol) in DMF (200 mL), was added NaH (60%; 1.73 g, 43.3 mmol) portion wise. Once the initial effervescence had subsided, the mixture was heated at 60° C. for 1 h, and then was cooled to rt. A solution of 6-chloronicotinonitrile (4.0 g, 28.9 mmol) in DMF (20 mL) was then added and the mixture was stirred for 16 h before quenching with saturated (satd.) aq. NaHCO$_3$ (50 mL) and brine (50 mL). A precipitate was formed and was collected by vacuum filtration to afford 3.67 g of the product. The filtrate was concentrated to half the volume and a second crop of precipitate was recovered. The precipitates were combined to give 5.64 g (76%) of an orange solid, which was used without further purification. MS (ESI): mass calcd for $C_{15}H_{21}N_3O$, 259.17; m/z found, 260.4 [M+H]$^+$. $^1$H NMR (400 MHz, CDCl$_3$): 8.46 (dd, J=2.3, 0.8, 1H), 7.77 (dd, J=8.6, 2.3, 1H), 6.80 (dd, J=8.6, 0.8, 1H), 4.34 (t, J=6.6, 2H), 2.96-2.82 (m, 2H), 2.25 (s, 3H), 1.92-1.68 (m, 7H), 1.37-1.34 (m, 2H), 0.89-0.81 (m, 2H).

General Procedure 6.

B. 6-[3-(1-Methyl-piperidin-4-yl)-propoxy]-pyridine-3-carbaldehyde. To a 0° C. solution of 6-[3-(1-methyl-piperidin-4-yl)-propoxy]-nicotinonitrile (640 mg, 2.47 mmol) in toluene (20 mL) was added 1.0 M DIBAL-H in hexanes (3.70 mL, 3.70 mmol) dropwise. The mixture was warmed to rt and stirred for 2 h (complete by TLC). Methanol was added (5 mL) followed by 1.0 M H$_2$SO$_4$ (10 mL). After stirring for 30 min the solution was neutralized with satd. aq. NaHCO$_3$, diluted with satd. aq. sodium potassium tartrate (10 mL), and stirred an additional 30 min. The reaction was extracted with CHCl$_3$ (3×50 mL) and the combined extracts were dried (Na$_2$SO$_4$), filtered, and concentrated, yielding the crude product, which was purified by Method 1 to afford 598 mg (92%) of a colorless oil. MS (ESI): mass calcd for $C_{15}H_{22}N_2O_2$, 262.17; m/z found, 263.1 [M+H]$^+$. $^1$H NMR (400 MHz, CDCl$_3$): 9.87 (br s, 1H), 8.53 (d, J=2.3, 1H), 7.98 (dd, J=8.6, 2.3, 1H), 6.74 (d, J=8.6, 1H), 4.34 (t, J=6.6, 2H), 2.78-2.26 (m, 2H), 2.19 (s, 3H), 1.85-1.62 (m, 7H), 1.35-1.16 (m, 4H).

C. 5-[4-(3,5-Dichloro-Phenyl)-5-methyl-1H-imidazol-2-yl]-2-[3-(1-methyl-piperidin-4-yl)-propoxy]-pyridine.
Preparation by the method described in General Procedure 3 using 6-[3-(1-methyl-piperidin-4-yl)-propoxy]-pyridine-3-carbaldehyde (70.0 mg, 0.26 mmol) gave 10 mg (8.4%) of the title compound. MS (ESI): mass calcd for $C_{24}H_{28}Cl_2N_4O$, 458.16; m/z found, 459.3 [M+H]$^+$. $^1$H NMR (400 MHz, CDCl$_3$): 9.36 (br s, 1H), 8.49 (s, 1H), 8.12 (dd, J=8.6, 2.3, 1H), 7.62 (s, 2H), 7.24 (s, 1H), 6.81 (d, J=8.6, 1H), 4.13 (t, J=6.6, 2H), 2.85-2.82 (m, 2H), 2.52, (s, 3H), 2.25 (s, 3H), 1.91-1.68 (m, 7H), 1.41-1.36 (m, 2H), 1.29-1.23 (m, 2H).

Compounds shown in Examples 28-31 were prepared using methods similar to those described in General Procedure 3, with the appropriate substituent changes.

Example 28

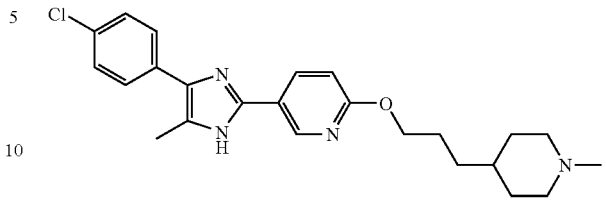

5-[4-(4-Chloro-phenyl)-5-methyl-1H-imidazol-2-yl]-2-[3-(1-methyl-piperidin-4-yl)-propoxy]-pyridine MS (ESI): mass calcd for $C_{24}H_{29}ClN_4O$, 424.20; m/z found, 425.4 [M+H]$^+$. $^1$H NMR (400 MHz, CDCl$_3$): 9.06 (br s, 1H), 8.51 (s, 1H), 8.13-8.11 (m, 1H), 7.61-7.65 (m, 2H), 7.42-7.36 (m, 2H), 6.81 (d, J=8.6, 1H), 4.13 (t, J=6.6, 2H), 2.86-2.83 (m, 2H), 2.52 (s, 3H), 2.25 (s, 3H), 1.93-1.70 (m, 7H), 1.42-1.26 (m, 4H).

Example 29

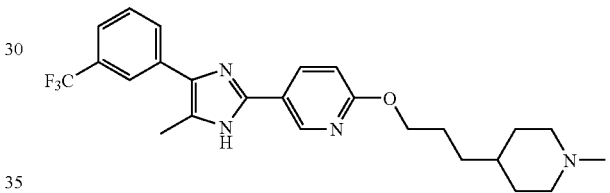

2-[3-(1-Methyl-piperidin-4-yl)-propoxy]-5-[5-methyl-4-(3-trifluoromethyl-phenyl)-1H-imidazol-2-yl]-pyridine $^1$H NMR (400 MHz, CDCl$_3$): 9.17 (br s, 1H), 8.52 (br s, 1H), 8.16-8.13 (m, 1H), 8.01-7.91 (m, 1H), 7.91-7.88 (m, 1H), 7.54-7.40 (m, 2H), 6.80 (d, J=8.6, 1H), 4.31 (t, J=6.6, 2H), 2.89-2.87 (m, 2H), 2.54, (s, 3H), 2.28 (s, 3H), 1.95-1.69 (m, 7H), 1.44-1.36 (m, 2H), 1.31-1.23 (m, 2H).

Example 30

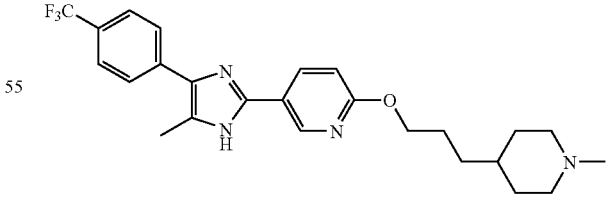

2-[3-(1-Methyl-piperidin-4-yl)-propoxy]-5-[5-methyl-4-(4-trifluoromethyl-phenyl)-1H-imidazol-2-yl]-pyridine $^1$H NMR (400 MHz, CDCl$_3$): 9.36 (br s, 1H), 8.53 (br s, 1H), 8.12 (d, J=8.6, 1H), 7.84 (d, J=7.8, 2H), 7.65 (d, J=7.8, 2H), 6.80 (d, J=8.6, 1H), 4.30 (t, J=6.6, 2H), 2.86-2.83 (m, 2H), 2.54, (s, 3H), 2.26 (s, 3H), 1.93-1.68 (m, 7H), 1.42-1.36 (m, 2H), 1.30-1.25 (m, 2H).

Example 31

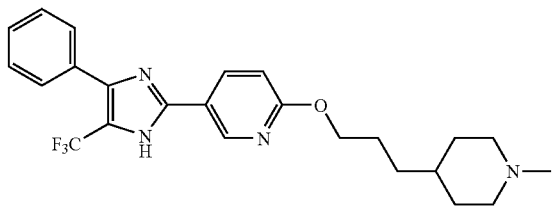

2-[3-(1-Methyl-piperidin-4-yl)-propoxy]-5-(4-phenyl-5-trifluoromethyl-1H-imidazol-2-yl)-pyridine MS (ESI): mass calcd for $C_{24}H_{27}F_3N_4O$, 444.21; m/z found, 445.4 [M+H]$^+$. $^1$H NMR (400 MHz, CDCl$_3$): 8.55 (d, J=2.3, 1H), 8.13 (dd, J=8.6, 2.3, 1H), 7.54-7.44 (m, 5H), 6.81 (d, J=8.6, 1H), 4.31 (t, J=6.6, 2H), 2.83-2.81 (m, 2H), 2.25, (s, 3H), 1.91-1.68 (m, 7H), 1.41-1.36 (m, 2H), 1.28-1.21 (m, 2H).

Example 32

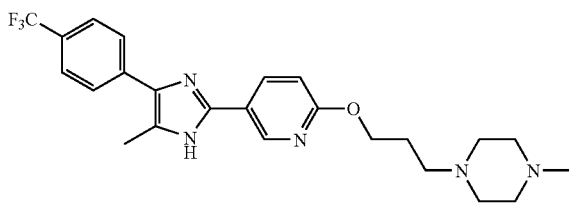

1-Methyl-4-(3-{5-[5-methyl-4-(4-trifluoromethyl-phenyl)-1H-imidazol-2-yl]-pyridin-2-yloxy}-propyl)-piperazine A. 6-[3-(4-Methyl-piperazin-1-yl)-propoxy]-nicotinonitrile. This compound was prepared by the method described in General Procedure 5 in Example 27 using 3-(4-methyl-piperazin-1-yl)-propan-1-ol (1.0 g, 6.32 mmol), 60% sodium hydride (379 mg, 9.48 mmol), and 6-chloronicotinonitrile (876 mg, 6.32 mmol). The reaction mixture was partitioned between satd. aq. NaHCO$_3$ (30 mL) and CHCl$_3$ (60 mL). The organic layer was dried (Na$_2$SO$_4$), filtered, and concentrated. Purification by Method 1 afforded 776 mg (47%) of a beige solid. MS (ESI): mass calcd for $C_{14}H_{20}N_4O$, 260.16; m/z found, 261.3 [M+H]$^+$. $^1$H NMR (400 MHz, CDCl$_3$): 8.47 (dd, J=2.3, 0.8, 1H), 7.77 (dd, J=8.6, 2.3, 1H), 6.80 (dd, J=8.6, 0.8, 1H), 4.41 (t, J=6.6, 2H), 2.76-2.35 (m, 10H), 2.29 (s, 3H), 2.01-1.95 (m, 2H).

B. 6-[3-(4-Methyl-piperazin-1-yl)-propoxy]-pyridine-3-carbaldehyde. This compound was prepared by the method described in General Procedure 6 in Example 27 using 6-[3-(4-methyl-piperazin-1-yl)-propoxy]-nicotinonitrile (486 mg, 1.86 mmol) and 1.0 M DIBAL-H in hexanes (2.79 mg, 2.79 mmol, 1.5 equiv). Purification by Method 1 afforded 225 mg (46%) of a colorless residue. MS (ESI): mass calcd for $C_{14}H_{21}N_3O_2$, 263.16; m/z found, 264.2 [M+H]$^+$. $^1$H NMR (400 MHz, CDCl$_3$): 9.94 (s, 1H), 8.61 (d, J=2.3, 1H), 8.06 (dd, J=8.6, 2.3, 1H), 6.82 (d, J=8.6, 1H), 4.46 (t, J=6.6, 2H), 2.64-2.33 (m, 10H), 2.29 (s, 3H), 2.03-1.96 (m, 2H).

C. 1-Methyl-4-(3-{5-[5-methyl-4-(4-trifluoromethyl-phenyl)-1H-imidazol-2-yl]-pyridin-2-yloxy}-propyl)-piperazine. Preparation by the method described in General Procedure 3 with appropriate substituent changes provided 13 mg (17%) of the title compound. MS (ESI): mass calcd for $C_{24}H_{28}F_3N_5O$, 459.22; m/z found, 460.4 [M+H]$^+$. $^1$H NMR (400 MHz, CDCl$_3$): 9.86 (br s, 1H), 8.51 (s, 1H), 8.09 (d, J=8.6, 1H), 7.84-7.74 (br s, 2H), 7.64 (d, J=7.8, 2H), 6.77 (d, J=8.6, 1H), 4.34 (t, J=6.6, 2H), 2.60-2.39 (m, 13H), 2.28 (s, 3H), 2.02-1.94 (m, 2H).

Example 33

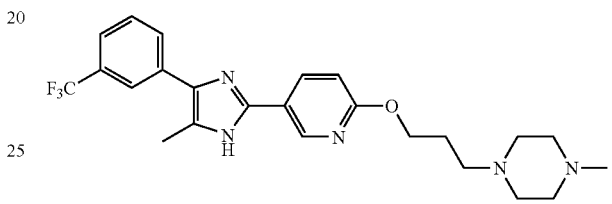

1-Methyl-4-(3-{5-[5-methyl-4-(3-trifluoromethyl-phenyl)-1H-imidazol-2-yl]-pyridin-2-yloxy}-propyl)-piperazine Preparation by the method described in General Procedure 3 with appropriate substituent changes afforded 7 mg (9%) of the title compound. MS (ESI): mass calcd for $C_{24}H_{28}F_3N_5O$, 459.22; m/z found, 460.4 [M+H]$^+$. $^1$H NMR (400 MHz, CDCl$_3$): 9.34 (br s, 1H), 8.51 (s, 1H), 8.14 (d, J=8.6, 1H), 8.04-7.83 (br s, 2H), 7.66-7.52 (m, 2H), 6.80 (d, J=8.6, 1H), 4.38 (t, J=6.6, 2H), 2.57-2.37 (m, 13H), 2.30 (s, 3H), 2.02-1.95 (m, 2H).

Example 34

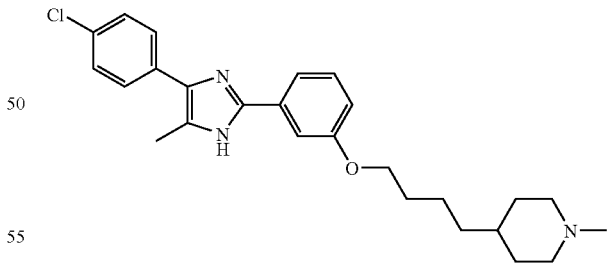

4-(4-{3-[4-(4-Chloro-phenyl)-5-methyl-1H-imidazol-2-yl]-phenoxy}-butyl)-1-methyl-piperidine A. 3-[4-(1-Methyl-piperidin-4-yl)-butoxy]-benzonitrile. To a 0° C. solution of 4-(1-methyl-piperidin-4-yl)-butan-1-ol (0.74 g, 4.37 mmol), 3-hydroxy-benzonitrile (0.52 g, 4.37 mmol), and 3 mmol/g polymer supported PPh$_3$ (2.30 g, 8.73 mmol) in THF (40 mL) was added diisopropyl azodicarboxylate (1.72 mL, 8.73 mmol) dropwise. After 6 h the mixture was filtered and concentrated. Purification by Method 1 afforded 840 mg (71%) of a yellow oil. MS (ESI): mass calcd for $C_{17}H_{24}N_2O$, 272.19; m/z found, 273.4 [M+H]$^+$. $^1$H NMR (400 MHz, CDCl$_3$): 7.38-7.33 (m, 1H), 7.24-7.20 (m, 1H), 7.14-7.09 (m, 2H), 3.96 (t, J=6.4, 2H), 2.88-2.80 (m, 2H), 2.26 (s, 3H), 1.94-1.84 (m, 2H), 1.82-1.73 (m, 2H), 1.72-1.64 (m, 2H), 1.52-1.42 (m, 2H), 1.34-1.17 (m, 5H).

B. 3-[4-(1-Methyl-piperidin-4-yl)-butoxy]-benzaldehyde. To a stirred solution of 3-[4-(1-methyl-piperidin-4-yl)-butoxy]-benzonitrile (0.84 g, 3.09 mmol) in toluene (5 mL) at 0° C. was added 1.5 M DIBAL-H in toluene (4.63 mL, 4.63 mmol). After 3 h, methanol (9 mL) and 1.0 M H$_2$SO$_4$ (10 mL) were added dropwise. After stirring for 30 min, the solution was neutralized with 1.0 M sodium hydroxide (10 mL) followed by addition of satd. aq. sodium potassium tartrate (40 mL) and CH$_2$Cl$_2$ (100 mL). After stirring for 30 min the solution was extracted with CHCl$_3$ (3×50 mL), washed with brine and dried over Na$_2$SO$_4$. Purification by Method 1 afforded 0.56 g (66%) of the title compound. $^1$H NMR (400 MHz, CDCl$_3$): 9.97 (s, 1H), 7.46-7.43 (m, 2H), 7.39-7.37 (m, 1H), 7.19-7.15 (m, 1H), 4.02 (t, J=6.6, 2H), 2.86-2.80 (m, 2H), 2.25 (s, 3H), 1.92-1.83 (m, 2H), 1.83-1.75 (m, 2H), 1.73-1.63 (m, 2H), 1.54-1.44 (m, 2H), 1.34-1.18 (m, 5H).

C. 4-(4-{3-[4-(4-Chloro-phenyl)-5-methyl-1H-imidazol-2-yl]-phenoxy}-butyl)-1-methyl-piperidine. Preparation using the method described in General Procedure 3 afforded 49 mg (28%) of the title compound. MS (ESI): mass calcd for $C_{26}H_{32}ClN_3O$, 437.22; m/z found, 438.4 [M+H]$^+$. $^1$H NMR (400 MHz, CDCl$_3$): 10.2 (br s, 1H), 7.64 (br s, 1H), 7.48-7.44 (m, 1H), 7.41-7.26 (m, 4H), 7.31-7.27 (m, 1H), 6.88-6.84 (m, 1H), 3.95-3.85 (m, 2H), 2.85-2.77 (m, 2H), 2.43 (s, 3H), 2.25 (s, 3H), 1.93-1.82 (m, 2H), 1.76-1.60 (m, 4H), 1.45-1.35 (m, 2H), 1.30-1.15 (m, 5H).

Example 35

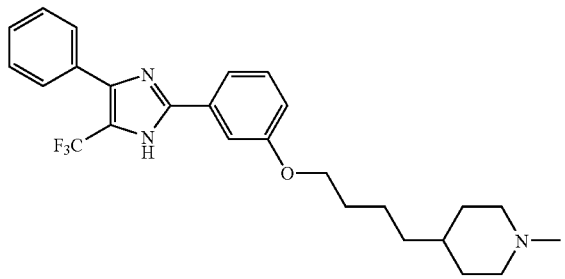

1-Methyl-4-{4-[3-(4-phenyl-5-trifluoromethyl-1H-imidazol-2-yl)-phenoxy]-butyl}-piperidine This compound was prepared using methods similar to those described in Example 34 with the appropriate substituent changes. MS (ESI): mass calcd for $C_{26}H_{30}F_3N_3O$, 457.23; m/z found 458.4 [M+H]$^+$. $^1$H NMR (400 MHz, CD$_3$OD): 7.51-7.28 (m, 8H), 6.96-6.91 (m, 1H), 3.93 (t, J=5.8, 2H), 2.79-2.71 (m, 2H), 2.23 (s, 3H), 1.88-1.80 (m, 2H), 1.77-1.68 (m, 2H), 1.66-1.56 (m, 2H), 1.46-1.11 (m, 7H).

Example 36

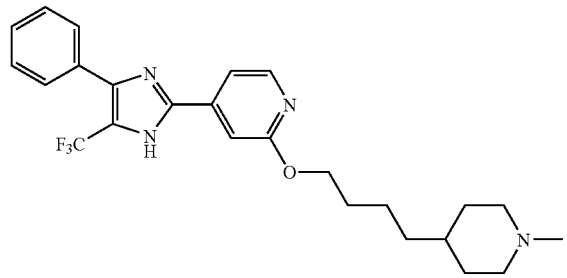

2-[4-(1-Methyl-piperidin-4-yl)-butoxy]-4-(4-phenyl-5-trifluoromethyl-1H-imidazol-2-yl)-pyridine A. 2-[4-(1-Methyl-piperidin-4-yl)-butoxy]-isonicotinonitrile. To a stirred solution of 4-(1-methyl-piperidin-4-yl)-butan-1-ol (1.0 g, 5.85 mmol) in DMF (12 mL) at 0° C. was added NaH (60%; 280 mg, 7.02 mmol). The mixture was warmed to rt for 1 h, then cooled to 0° C. A solution of 2-chloro-isonicotinonitrile (810 mg, 5.85 mmol) in DMF (4 mL) was added dropwise. The mixture was stirred at rt for 18 h, and then was diluted with water (5 mL) and satd. aq. NaHCO$_3$ (25 mL). The mixture was extracted with CHCl$_3$ (3×25 mL), dried (Na$_2$SO$_4$), filtered, and. Purification by Method 1 afforded 440 mg (28%) of a yellow oil. MS (ESI): mass calcd for $C_{16}H_{23}N_3O$, 273.18; m/z found, 274.4 [M+H]$^+$.

B. 2-[4-(1-Methyl-piperidin-4-yl)-butoxy]-pyridine-4-carbaldehyde. To a stirred solution of 2-[4-(1-methyl-piperidin-4-yl)-butoxy]-isonicotinonitrile (0.44 g, 1.61 mmol) in toluene (5 mL) at 0° C. was added a 1.5 M DIBAL-H in toluene (2.41 mL, 2.41 mmol). The reaction mixture was allowed to warm to rt. After 3 h, methanol (8 mL) and 1.0 M H$_2$SO$_4$ (5 mL) were added dropwise. After 30 min, the mixture was neutralized with 1.0 M NaOH (10 mL) followed by addition of satd. aq. sodium potassium tartrate (40 mL) and CH$_2$Cl$_2$ (100 mL). After 30 min the mixture was extracted with CHCl$_3$ (3×50 mL) and washed with brine. The organic layer was dried (Na$_2$SO$_4$), filtered, and concentrated. Purification of the mixture by Method 1 afforded 318 mg (64%) of the title compound. $^1$H NMR (400 MHz, CDCl$_3$): 10.0 (s, 1H), 8.34 (d, J=5.3, 1H), 7.28 (d, J=1.3, 1H), 7.14-7.12 (m, 1H), 4.33 (t, J=6.6, 2H), 2.87-2.80 (m, 2H), 2.25 (s, 3H), 1.93-1.65 (m, 6H), 1.52-1.42 (m, 2H), 1.35-1.07 (m, 5H).

C. 2-[4-(1-Methyl-piperidin-4-yl)-butoxy]-4-(4-phenyl-5-trifluoromethyl-1H-imidazol-2-yl)-pyridine. Preparation according to the method described in General Procedure 3 afforded 27.9 mg (36%) of the title compound. MS (ESI): mass calcd for $C_{25}H_{29}F_3N_4O$, 458.23; m/z found, 459.4 [M+H]$^+$. $^1$H NMR (400 MHz, CD$_3$OD): 8.20 (d, J=5.3, 0.5, 1H), 7.61-7.54 (m, 2H), 7.54-7.45 (m, 4H), 7.39-7.35 (m, 1H), 4.3 (t, J=6.4, 2H), 2.95-2.83 (m, 2H), 2.28 (s, 3H), 2.10-1.99 (m, 2H), 1.84-1.66 (m, 4H), 1.56-1.43 (m, 2H), 1.39-1.14 (m, 5H).

Example 37

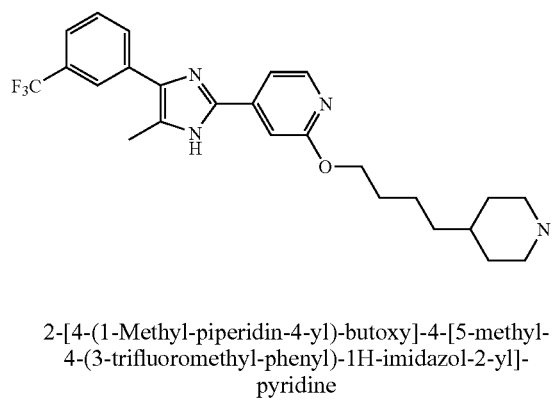

2-[4-(1-Methyl-piperidin-4-yl)-butoxy]-4-[5-methyl-4-(3-trifluoromethyl-phenyl)-1H-imidazol-2-yl]-pyridine This compound was prepared using methods similar to those described in Example 36 with the appropriate substituent changes. MS (ESI): mass calcd for $C_{26}H_{31}F_3N_4O$, 472.24; m/z found, 473.4 [M+H]$^+$. $^1$H NMR (400 MHz, CD$_3$OD): 8.16 (d, J=5.3, 1H), 7.95 (m, 2H), 7.91-7.86 (m, 2H), 7.45 (dd, J=5.5, 1.5, 1H), 7.30-7.26 (m, 1H), 4.29 (t, J=6.3, 2H), 2.89-2.80 (m, 2H), 2.49 (s, 3H), 2.25 (s, 3H), 2.03-1.92 (m, 2H), 1.82-1.66 (m, 4H), 1.55-1.44 (m, 2H), 1.36-1.16 (m, 5H).

Example 38

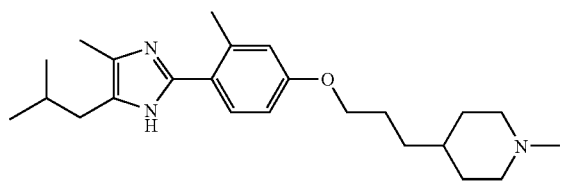

4-{3-[4-(5-Isobutyl-4-methyl-1H-imidazol-2-yl)-3-methyl-phenoxy]-propyl}-1-methyl-piperidine This compound was prepared using methods similar to those described in Example 14 with the appropriate substituent changes. MS (ESI): mass calcd for $C_{24}H_{37}N_3O$, 383.29; m/z found, 384.5 [M+H]$^+$. $^1$H NMR (400 MHz, CD$_3$OD): 7.29 (d, J=8.3, 1H), 6.83-6.74 (m, 2H), 3.97 (t, J=6.6, 2H), 2.91-2.81 (m, 2H), 2.40 (d, J=7.3, 2H), 2.36 (s, 3H), 2.26 (s, 3H), 2.16 (s, 3H), 2.06-1.62 (m, 7H), 1.49-1.16 (m, 5H), 0.93 (d, J=6.8, 6H).

Example 39

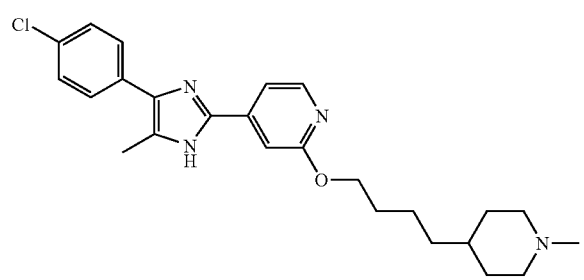

4-[4-(4-Chloro-phenyl)-5-methyl-1H-imidazol-2-yl]-2-[4-(1-methyl-piperidin-4-yl)-butoxy]-pyridine This compound was prepared using methods similar to those described in Example 36 with the appropriate substituent changes. MS (ESI): mass calcd for $C_{25}H_{31}ClN_4O$, 438.22; m/z found, 439.4 [M+H]$^+$. $^1$H NMR (400 MHz, CD$_3$OD): 8.18 (d, J=5.6, 1H), 7.67-7.61 (m, 2H), 7.49-7.44 (m, 3H), 7.32-7.30 (m, 1H), 4.35-4.29 (m, 2H), 2.99-2.91 (m, 2H), 2.47 (s, 3H), 2.34 (s, 3H), 2.18-2.08 (m, 2H), 1.84-1.22 (m, 11H).

Example 40

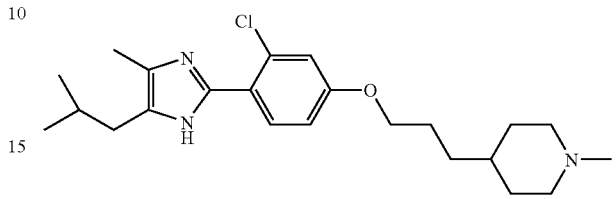

4-{3-[3-Chloro-4-(5-isobutyl-4-methyl-1H-imidazol-2-yl)-phenoxy]-propyl}-1-methyl-piperidine This compound was prepared using methods similar to those described in Example 14 with the appropriate substituent changes. MS (ESI): mass calcd for $C_{23}H_{34}ClN_3O$, 403.24; m/z found, 404.5 [M+H]$^+$. $^1$H NMR (400 MHz, CDCl$_3$): 9.91-9.60 (br s, 1H), 8.16-8.11 (m, 1H), 6.92-6.83 (m, 2H), 3.97-3.92 (m, 2H), 2.88-2.81 (m, 2H), 2.50-2.38 (m, 2H), 2.27-2.20 (m, 6H), 2.08-1.66 (m, 7H), 1.43-1.18 (m, 5H), 0.99-0.89 (m, 6H).

Example 41

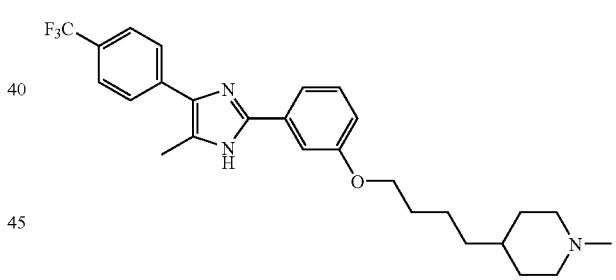

1-Methyl-4-(4-{3-[5-methyl-4-(4-trifluoromethyl-phenyl)-1H-imidazol-2-yl]-phenoxy}-butyl)-piperidine This compound was prepared using methods similar to those described in Example 36 with the appropriate substituent changes. MS (ESI): mass calcd for $C_{27}H_{32}F_3N_3O$, 471.25; m/z found 472.4 [M+H]$^+$. $^1$H NMR (400 MHz, CDCl$_3$): 9.87 (s, 1H), 7.92-7.50 (m, 4H), 7.48-7.45 (m, 1H), 7.40-7.36 (m, 1H), 7.34-7.28 (m, 1H), 6.89 (dd, J=8.1, 2.0, 1H), 3.99-3.91 (m, 2H), 2.86-2.79 (m, 2H), 2.50 (s, 3H), 2.25 (s, 3H), 1.91-1.85 (m, 2H), 1.78-1.60 (m, 4H), 1.48-1.37 (m, 2H), 1.32-1.15 (m, 5H).

Examples 42-45 were prepared using methods similar to those described in Example 1 with the appropriate substituent changes.

Example 42

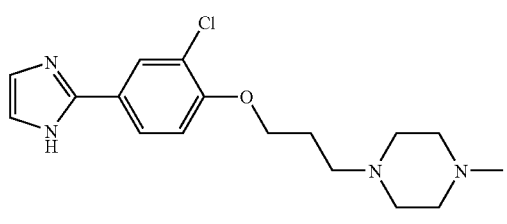

1-{3-[2-Chloro-4-(1H-imidazol-2-yl)-phenoxy]-propyl}-4-methyl-piperazine

MS (ESI): mass calcd for $C_{17}H_{23}ClN_4O$, 334.16; m/z found, 335.3 [M+H]$^+$. $^1$H NMR (400 MHz, CD$_3$OD): 7.89 (d, J=2.2, 1H), 7.74 (dd, J=8.6, 2.2, 1H), 7.15 (d, J=8.6, 1H), 7.09 (br s, 2H), 4.16 (t, J=6.0, 2H), 2.75-2.35 (m, 10H), 2.29 (s, 3H), 2.06-2.02 (m, 2H).

Example 43

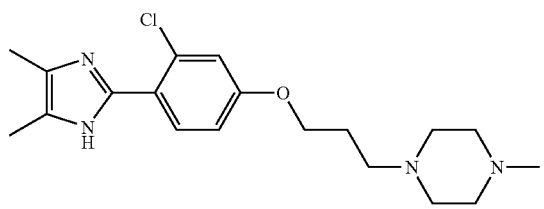

1-{3-[3-Chloro-4-(4,5-dimethyl-1H-imidazol-2-yl)-phenoxy]-propyl}-4-methyl-piperazine MS (ESI): mass calcd for $C_{19}H_{27}ClN_4O$, 362.19; m/z found, 363.4 [M+H]$^+$. $^1$H NMR (400 MHz, CD$_3$OD): 7.54 (d, J=8.7, 1H), 7.05 (d, J=2.5, 1H), 6.93 (dd, J=8.5, 2.5, 1H), 4.07 (t, J=6.1, 2H), 2.75-2.35 (m, 10H), 2.29 (s, 3H), 2.17 (s, 6H), 2.00-1.98 (m, 2H).

Example 44

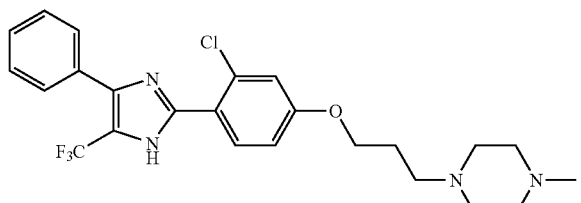

1-{3-[3-Chloro-4-(4-phenyl-5-trifluoromethyl-1H-imidazol-2-yl)-phenoxy]-propyl}-4-methyl-piperazine MS (ESI): mass calcd for $C_{24}H_{26}ClF_3N_4O$, 478.17; m/z found, 479.1 [M+H]$^+$. $^1$H NMR (400 MHz, CD$_3$OD): 7.61-7.57 (m, 3H), 7.53-7.45 (m, 3H), 7.15 (d, J=2.5, 1H), 7.03 (dd, J=8.7, 2.5, 1H), 4.11 (t, J=6.1, 2H), 2.75-2.35 (m, 10H), 2.31 (s, 3H), 2.04-2.00 (m, 2H).

Example 45

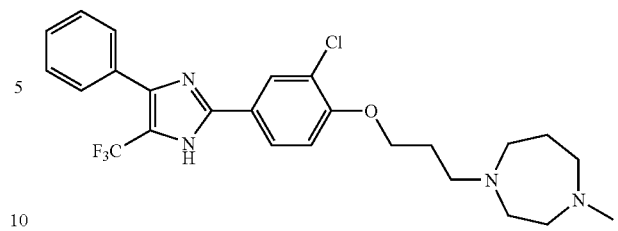

1-{3-[2-Chloro-4-(4-phenyl-5-trifluoromethyl-1H-imidazol-2-yl)-phenoxy]-propyl}-4-methyl-[1,4]diazepane MS (ESI): mass calcd for $C_{25}H_{28}ClF_3N_4O$, 492.19; m/z found, 493.1 [M+H]$^+$. $^1$H NMR (400 MHz, CD$_3$OD): 7.91 (d, J=2.2, 1H), 7.76 (dd, J=8.6, 2.2, 1H), 7.47-7.33 (m, 5H), 7.05 (d, J=8.7, 1H), 4.05 (t, J=6.0, 2H), 2.71-2.60 (m, 10H), 2.26 (s, 3H), 1.91-1.88 (m, 2H), 1.75-1.72 (m, 2H).

Examples 46-47 were prepared using methods similar to those described in Example 14 with the appropriate substituent changes.

Example 46

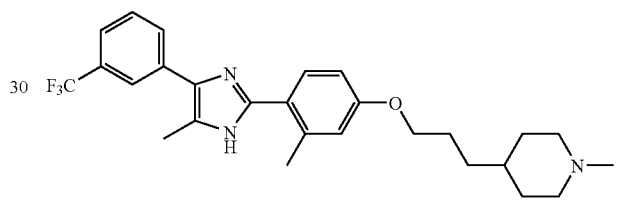

1-Methyl-4-(3-{3-methyl-4-[5-methyl-4-(3-trifluoromethyl-phenyl)-1H-imidazol-2-yl]-phenoxy}-propyl)-piperidine MS (ESI): mass calcd for $C_{27}H_{32}F_3N_3O$, 471.25; m/z found, 472.4 [M+H]$^+$. $^1$H NMR (400 MHz, CD$_3$OD): 7.94-7.87 (m, 2H), 7.63-7.54 (m, 2H), 7.42 (d, J=8.4, 1H), 6.88-6.82 (m, 2H), 4.01 (t, J=6.3, 2H), 2.96-2.82 (m, 2H), 2.49 (s, 3H), 2.47 (s, 3H), 2.28 (s, 3H), 2.09-2.00 (m, 2H), 1.88-1.72 (m, 4H), 1.52-1.42 (m, 2H), 1.40-1.21 (m, 3H).

Example 47

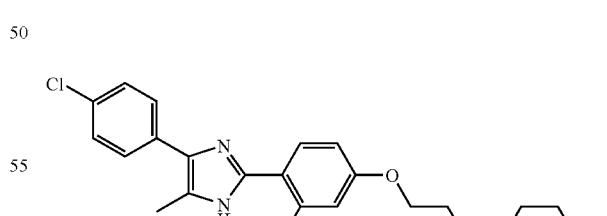

4-(3-{4-[4-(4-Chloro-phenyl)-5-methyl-1H-imidazol-2-yl]-3-methyl-phenoxy}-propyl)-1-methyl-piperidine MS (ESI): mass calcd for $C_{26}H_{32}ClN_3O$, 437.22; m/z found, 438.4 [M+H]$^+$. $^1$H NMR (400 MHz, CD$_3$OD): 7.60-

7.56 (m, 2H), 7.43-7.37 (m, 3H), 6.86 (d, J=2.4, 1H), 6.82 (dd, J=8.5, 2.5, 1H), 4.00 (t, J=6.4, 2H), 2.93-2.83 (m, 2H), 2.45 (s, 3H), 2.44 (s, 3H), 2.28 (s, 3H), 2.08-1.96 (m, 2H), 1.83-1.72 (m, 4H), 1.49-1.39 (m, 2H), 1.38-1.20 (m, 3H).

Example 48

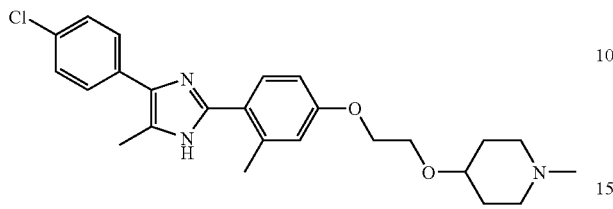

4-(2-{4-[4-(4-Chloro-phenyl)-5-methyl-1H-imidazol-2-yl]-3-methyl-phenoxy}-ethoxy)-1-methyl-piperidine The title compound was prepared using methods similar to those described in General Procedure 3 using 2-methyl-4-[2-(1-methyl-piperidin-4-yloxy)-ethoxy]-benzaldehyde. MS (ESI): mass calcd for $C_{25}H_{30}ClN_3O_2$, 439.98; m/z found, 440.3 [M+H]$^+$. $^1$H NMR (400 MHz, CD$_3$OD): 7.62-7.52 (m, 2H), 7.43-7.33 (m, 3H), 6.91-6.80 (m, 2H), 4.17-4.07 (m, 2H), 3.86-3.76 (m, 2H), 3.48 (br s, 1H), 2.78-2.63 (m, 2H), 2.44 (s, 3H), 2.42 (s, 3H), 2.30-2.15 (m, 5H), 1.98-1.86 (m, 2H), 1.72-1.58 (m, 2H).

Examples 49-68 are prepared using methods similar to those described in Examples 1-48.

Example 49

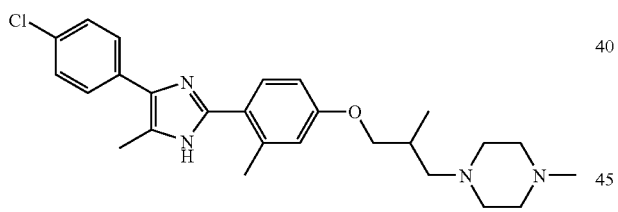

1-(3-{4-[4-(4-Chloro-phenyl)-5-methyl-1H-imidazol-2-yl]-3-methyl-phenoxy}-2-methyl-propyl)-4-methyl-piperazine Example 50

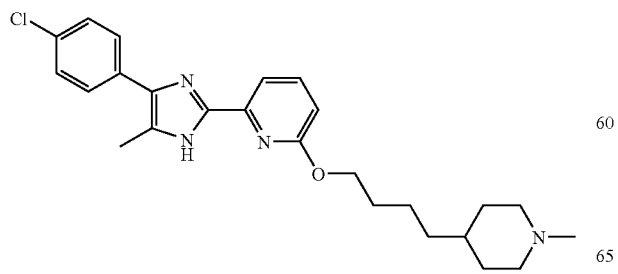

2-[4-(4-Chloro-phenyl)-5-methyl-1H-imidazol-2-yl]-6-[4-(1-methyl-piperidin-4-yl)-butoxy]-pyridine Example 51

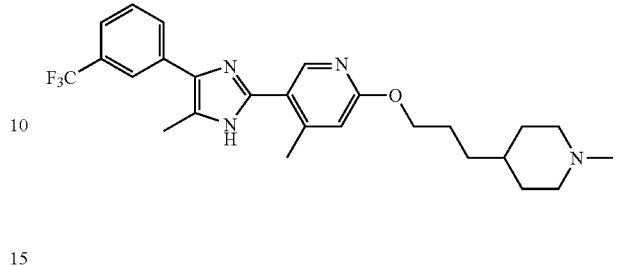

4-Methyl-2-[3-(1-methyl-piperidin-4-yl)-propoxy]-5-[5-methyl-4-(3-trifluoromethyl-phenyl)-1H-imidazol-2-yl]-pyridine Example 52

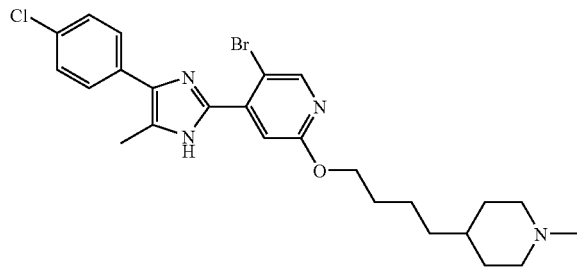

5-Bromo-4-[4-(4-chloro-phenyl)-5-methyl-1H-imidazol-2-yl]-2-[4-(1-methyl-piperidin-4-yl)-butoxy]-pyridine Example 53

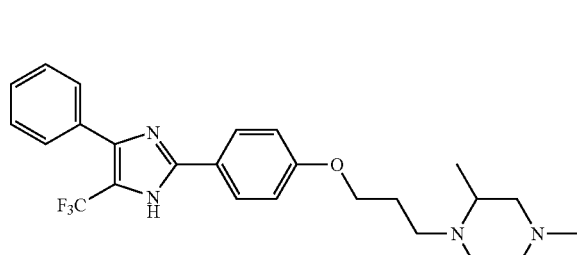

2,4-Dimethyl-1-{3-[4-(4-phenyl-5-trifluoromethyl-1H-imidazol-2-yl)-phenoxy]-propyl}-piperazine Example 54

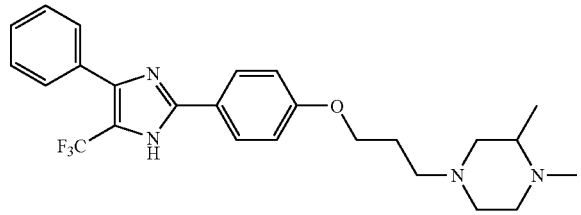

1,2-Dimethyl-4-{3-[4-(4-phenyl-5-trifluoromethyl-1H-imidazol-2-yl)-phenoxy]-propyl}-piperazine Example 55

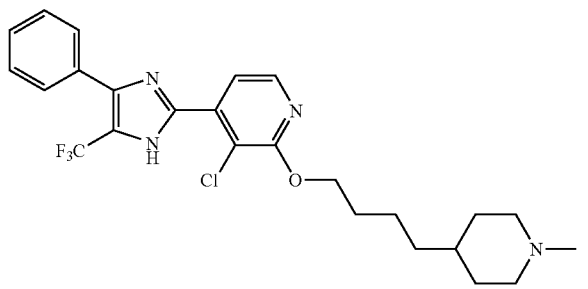

3-Chloro-2-[4-(1-methyl-piperidin-4-yl)-butoxy]-4-(4-phenyl-5-trifluoromethyl-1H-imidazol-2-yl)-pyridine Example 56

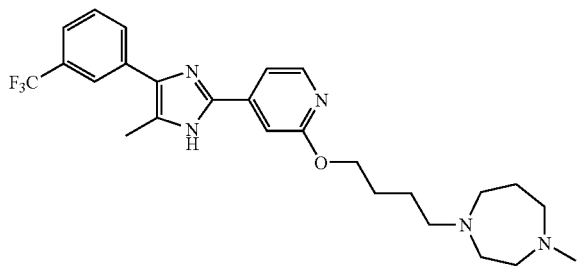

1-Methyl-4-(4-{4-[5-methyl-4-(3-trifluoromethyl-phenyl)-1H-imidazol-2-yl]-pyridin-2-yloxy}-butyl)-[1,4]diazepane Example 57

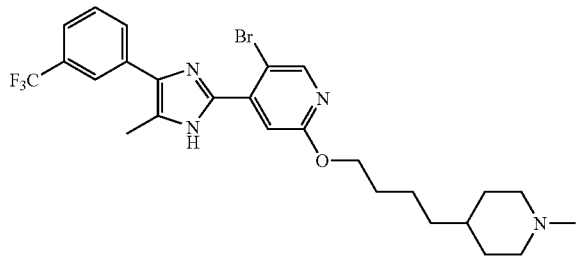

5-Bromo-2-[4-(1-methyl-piperidin-4-yl)-butoxy]-4-[5-methyl-4-(3-trifluoromethyl-phenyl)-1H-imidazol-2-yl]-pyridine Example 58

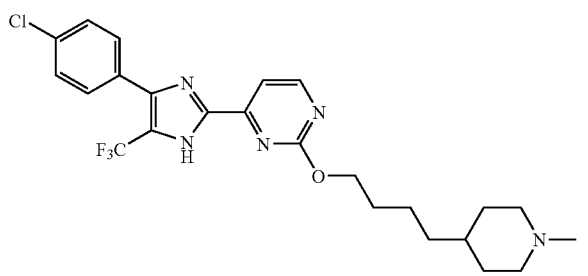

4-[4-(4-Chloro-phenyl)-5-trifluoromethyl-1H-imidazol-2-yl]-2-[4-(1-methyl-piperidin-4-yl)-butoxy]-pyrimidine Example 59

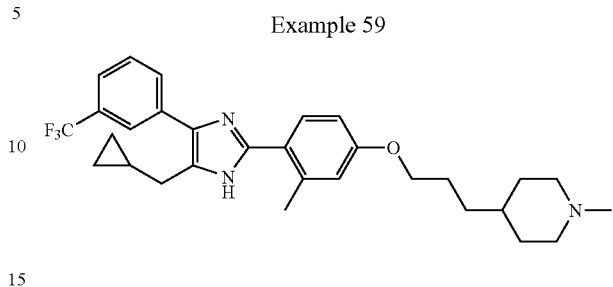

4-(3-{4-[5-Cyclopropylmethyl-4-(3-trifluoromethyl-phenyl)-1H-imidazol-2-yl]-3-methyl-phenoxy}-propyl)-1-methyl-piperidine Example 60

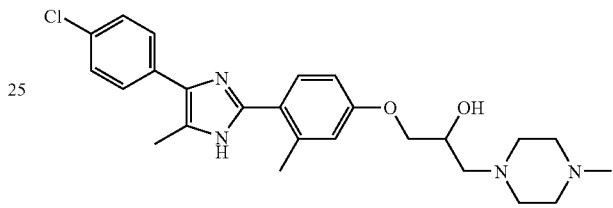

1-{4-[4-(4-Chloro-phenyl)-5-methyl-1H-imidazol-2-yl]-3-methyl-phenoxy}-3-(4-methyl-piperazin-1-yl)-propan-2-ol Example 61

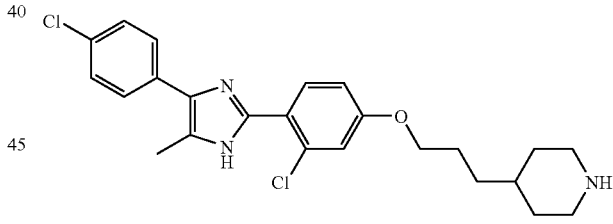

4-(3-{3-Chloro-4-[4-(4-chloro-phenyl)-5-methyl-1H-imidazol-2-yl]-phenoxy}-propyl)-piperidine Example 62

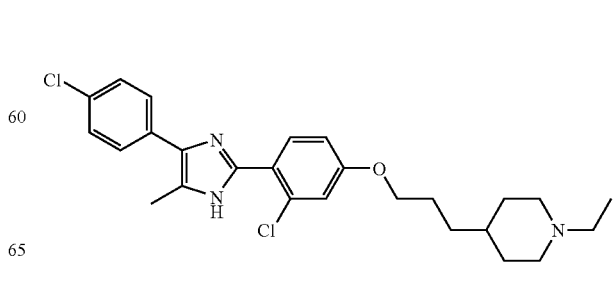

49

4-(3-{3-Chloro-4-[4-(4-chloro-phenyl)-5-methyl-1H-imidazol-2-yl]-phenoxy}-propyl)-1-ethyl-piperidine Example 63

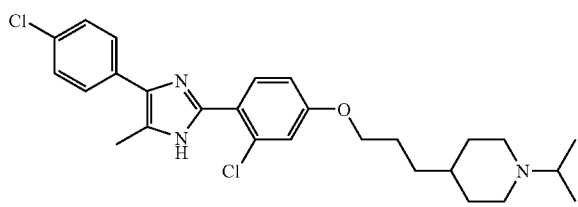

4-(3-{3-Chloro-4-[4-(4-chloro-phenyl)-5-methyl-1H-imidazol-2-yl]-phenoxy}-propyl)-1-isopropyl-piperidine Example 64

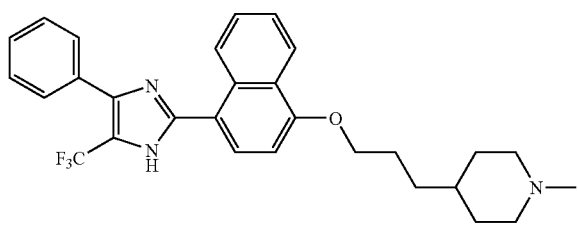

1-Methyl-4-{3-[4-(4-phenyl-5-trifluoromethyl-1H-imidazol-2-yl)-naphthalen-1-yloxy]-propyl}-piperidine Example 65

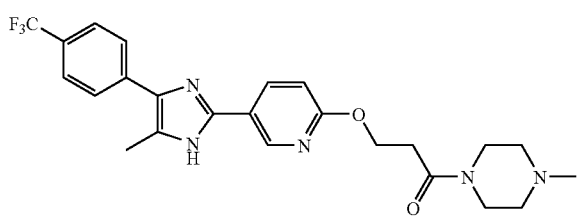

1-(4-Methyl-piperazin-1-yl)-3-{5-[5-methyl-4-(4-trifluoromethyl-phenyl)-1H-imidazol-2-yl]-pyridin-2-yloxy}-propan-1-one Example 66

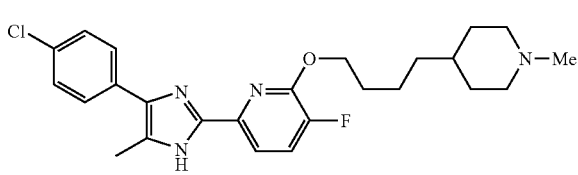

50

6-[4-(4-Chloro-phenyl)-5-methyl-1H-imidazol-2-yl]-3-fluoro-2-[4-(1-methyl-piperidin-4-yl)-butoxy]-pyridine Example 67

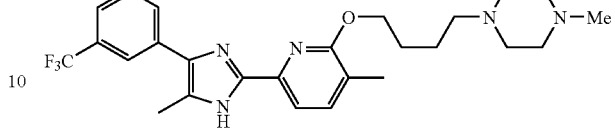

1-Methyl-4-(4-{3-methyl-6-[5-methyl-4-(3-trifluoromethyl-phenyl)-1H-imidazol-2-yl]-pyridin-2-yloxy}-butyl)-piperazine Example 68

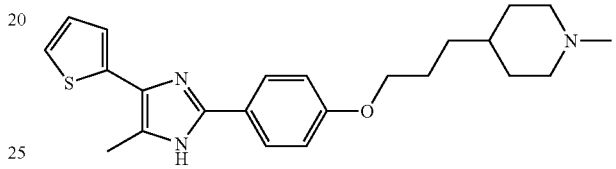

1-Methyl-4-{3-[4-(5-methyl-4-thiophen-2-yl-1H-imidazol-2-yl)-phenoxy]-propyl}-piperidine Example 69

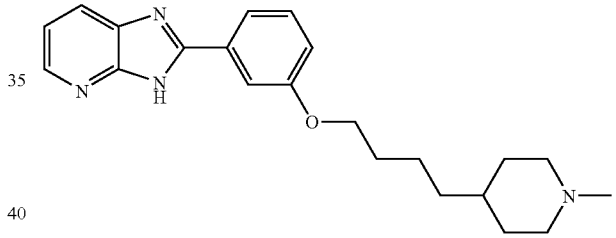

2-{3-[4-(1-Methyl-piperidin-4-yl)-butoxy]-phenyl}-3H-imidazo[4,5-b]pyridine

The title compound was prepared using methods similar to those described in Example 1. MS (ESI): mass calcd for $C_{22}H_{28}N_4O$, 364.48; m/z found, 365.4 [M+H]$^+$. $^1$H NMR (400 MHz, CD$_3$OD): 8.30-8.22 (dd, J=4.9, 1.5, 1H), 7.95-7.86 (dd, J=8.0, 1.4, 1H), 7.67-7.57 (m, 2H), 7.42-7.30 (m, 1H), 7.26-7.16 (m, 1H), 7.05-6.95 (dd, J=8.2, 2.4, 1H), 4.07-3.93 (t, J=6.3, 2H), 2.84-2.70 (m, 2H), 2.18-2.12 (s, 3H), 2.00-1.82 (m, 2H), 1.79-1.56 (m, 4H), 1.52-1.37 (m, 2H), 1.32-1.01 (m, 5H).

Biological Examples

Binding Assay on Recombinant Human Histamine H$_4$ Receptor

SK-N-MC cells or COS7 cells were transiently transfected with pH4R and grown in 150 cm$^2$ tissue culture dishes. Cells were washed with saline solution, scraped with a cell scraper and collected by centrifugation (1000 rpm, 5 min). Cell membranes were prepared by homogenization of the cell pellet in 20 mM Tris-HCl with a polytron tissue homogenizer for 10 sec at high speed. Homogenate was centrifuged at 1000 rpm for 5 min at 4° C. The supernatant was then collected and centrifuged at 20,000×g for 25 min at 4° C. The final pellet was resuspended in 50 mM Tris-HCl. Cell membranes were incubated with $^3$H-histamine (5-70 nM) in the presence or absence of excess histamine (10,000 nM). Incubation occurred at room temperature for 45 min. Membranes were harvested by rapid filtration over Whatman GF/C filters and washed 4 times with ice-cold 50 mM Tris HCl. Filters were then dried, mixed with scintillant and counted for radioactivity. SK-N-MC or COS7 cells expressing human histamine $H_4$ receptor were used to measure the affinity of binding of other compounds and their ability to displace H-ligand binding by incubating the above-described reaction in the presence of various concentrations of inhibitor or compound to be tested. For competition binding studies using $^3$H-histamine, $K_i$ values were calculated, based on an experimentally determined $K_D$ value of 5 nM and a ligand concentration of 5 nM, according to Y.-C. Cheng and W. H. Prusoff (*Biochem. Pharmacol.* 1973, 22(23):3099-3108): $K_i (IC_{50})/(1+([L]/(K_D))$.

Binding Assay Results

TABLE 1

| EX | $K_i$ (nM) |
| --- | --- |
| 1 | 14 |
| 2 | 39 |
| 3 | 244 |
| 4 | 44 |
| 5 | 24 |
| 6 | 29 |
| 7 | 21 |
| 8 | 60 |
| 9 | 11 |
| 10 | 6 |
| 11 | 70 |
| 12 | 65 |
| 13 | 32 |
| 14 | 32 |
| 15 | 38 |
| 16 | 165 |
| 17 | 52 |
| 18 | 45 |
| 19 | 22 |
| 20 | 39 |
| 21 | 37 |
| 22 | 29 |
| 23 | 155 |
| 24 | 69 |
| 25 | 100 |
| 26 | 300 |
| 27 | 290 |
| 28 | 72 |
| 29 | 42 |
| 30 | 64 |
| 31 | 186 |
| 32 | 230 |
| 33 | 63 |
| 34 | 33 |
| 35 | 57 |
| 36 | 54 |
| 37 | 174 |
| 38 | 230 |
| 39 | 230 |
| 40 | 93 |
| 41 | 250 |
| 42 | 1963 |
| 43 | 2510 |
| 44 | 20 |
| 45 | 79 |
| 46 | 16 |
| 47 | 33 |
| 48 | 620 |
| 69 | 1413 |

Mast Cell Chemotaxis Assay

Mast cell accumulation in mucosal epithelia is a well-known characteristic of allergic rhinitis and asthma. In addition, it is known that mast cell numbers increase in a number of inflammatory conditions. Some of this is due to chemotaxis of mast cells to the sites of inflammation. This chemotaxis to specific agents can be mimicked in vitro. Transwells (Costar, Cambridge, Mass.) of a pore size 8 μm were coated with 100 μL of 100 ng/mL human fibronectin (Sigma) for 2 h at room temperature. After removal of the fibronectin, 600 μL of RPMI with 5% BSA, in the presence of 10 μM histamine, was added to the bottom chamber. To test the various histamine receptor (HR) antagonists, 10 μM and/or 1 μM solutions of the test compounds were added to the top and bottom chambers. Mast cells (2×10$^5$/well) were added to the top chamber. The plates were incubated for 3 h at 37° C. Transwells were removed and the cells in the bottom chamber were counted for sixty seconds using a flow cytometer. Histamine receptor (HR) inhibition data were thus obtained.

Cell-Type Distribution of $H_4$ Expression

RNA was prepared from the different cells using an RNeasy kit (Qiagen, Valencia, Calif.) according to the manufacturer's instructions. Total RNA was extracted from purified human cells using the RNeasy kit (Qiagen, Valencia, Calif.) and reverse transcribed to cDNA using the RT reaction kit (Invitrogen) according to the manufacturer's instructions. $H_4$ receptor RNA was detected by RT-PCR using human $H_4$ receptor-specific primers 5'-ATGCCAGATACTAATAG-CACA (SEQ ID NO.:1) and 5'-CAGTCGGTCAGTATCT-TCT (SEQ ID NO.:2). The amplified PCR band for $H_4$ receptor is 1170 bp.

Results

The RT-PCR results indicated that the $H_4$ receptor is expressed on mast cells, dendritic cells, basophils, and eosinophils. These positive results are consistent with the published literature (e.g. Oda et al., Nguyen et al., and Morse et al. in the Background section). Accumulation of mast cells and eosinophils in affected tissues is one of the principal characteristics of allergic rhinitis and asthma. Since $H_4$ receptor expression is found in these cell types, $H_4$ receptor signalling is likely to mediate the infiltration of mast cells and eosinophils in response to histamine. The following table reports the Cell-type Distribution of $H_4$ Expression by RT-PCR. A (+) indicates the presence of $H_4$ receptors; a (−) indicates the absence of $H_4$ receptors.

TABLE 2

| Species | Cell Type | $H_4$ |
| --- | --- | --- |
| Human | Eosinophils | + |
|  | Immature Dendritic Cells | + |
|  | Mature Dendritic Cells | + |
|  | Mast Cells | + |
|  | Basophils | + |
|  | CD14$^+$ Monocytes | − |
|  | CD4$^+$ T Cells | + |
|  | CD8$^+$ T Cells | − |
|  | B Cells | − |
|  | Neutrophils | − |
| Mouse/(Rat) | Eosinophils | + |
|  | Peritoneal Mast Cells (Rat) | + |
|  | Bone Marrow-Derived Mast Cells | + |
|  | Immature Dendritic Cells | + |
|  | Mature Dendritic Cells | + |
|  | Bone Marrow-Derived Macrophages | − |
|  | Peritoneal Macrophages | − |
|  | CD4$^+$ T Cells | − |
|  | CD8$^+$ T Cells | − |
|  | B Cells | − |

The Inhibition of Eosinophil Shape Change by Histamine $H_4$ Receptor Antagonists Eosinophil accumulation in sites of allergic reaction is a well-known characteristic of allergic rhinitis and asthma. This example demonstrates that histamine $H_4$ receptor antagonists can block the shape change response in human eosinophils in response to histamine. Shape change is a cellular characteristic that precedes eosinophil chemotaxis.

Methods

Human granulocytes were isolated from human blood by a Ficoll gradient. The red blood cells were lysed with 5-10× Qiagen lysis buffer at room temperature for 5-7 min. Granulocytes were harvested and washed once with FACS buffer. The cells were resuspended at a density of $2\times10^6$ cells/mL in reaction buffer. To test inhibition by specific histamine receptor antagonists, 90 µL of the cell suspension (~$2\times10^5$ cells) was incubated with 10 µM of one of the various test compound solutions. After 30 min, 11 µL of one of the various concentrations of histamine was added. Ten minutes later the cells were transferred to ice and fixed with 250 µL of ice-cold fixative buffer (2% formaldehyde) for 1 min. The shape change was quantitated using a gated autofluorescence forward scatter assay (GAFS) (S. A. Bryan et al., *Am. J. Respir. Crit. Care Med.* 2002, 165(12):1602-1609).

Results—Histamine Mediates Eosinophil Shape Change Through $H_4$ Receptor

The change in shape of eosinophils is due to cytoskeletal changes that precede chemotaxis and thus is a measure of chemotaxis. The data in the following table show that histamine induces a dose-dependent shape change in eosinophils. Histamine receptor (HR) antagonists were used to sort out which histamine receptor is responsible for the shape change. Antagonists specific for the histamine $H_1$ receptor (diphenhydramine) or the $H_2$ receptor (ranatidine) did not alter the histamine-induced shape change. However, a dual $H_3/H_4$ antagonist (thioperamide) and a specific histamine $H_4$ receptor antagonist ((5-chloro-1H-indol-2-yl)-(4-methyl-piperazin-1-yl)-methanone, $K_i$=5 nM) inhibited histamine-induced eosinophil shape change with an $IC_{50}$ of 1.5 and 0.27 µM, respectively.

TABLE 3

| | Fold Change | | | | |
|---|---|---|---|---|---|
| Histamine (µM): | 10 | 1 | 0.1 | 0.01 | 0 |
| No HR Antagonist | 1.34 | 1.31 | 1.21 | 1.01 | 1.00 |
| 10 µM $H_4$ Antagonist | 1.09 | 1.05 | 1.05 | 1.01 | 1.00 |
| 10 µM Thiop | 1.08 | 1.05 | 1.01 | 1.04 | 1.00 |
| 10 µM Diphen | 1.63 | 1.50 | 1.18 | 1.03 | 1.00 |
| 10 µM Ranat | 1.64 | 1.49 | 1.21 | 1.04 | 1.00 |

The Inhibition of Eosinophil Chemotaxis by Histamine $H_4$ Receptor Antagonists

Eosinophil accumulation in sites of allergic reaction is a well-known characteristic of allergic rhinitis and asthma. Eosinophils were purified from human blood with standard methods. Chemotaxis assays were carried out using transwells (Costar, Cambridge, Mass.) of a pore size 5 µm coated with 100 µL of 100 ng/mL human fibronectin (Sigma) for 2 h at room temperature. After removal of the fibronectin, 600 µL of RPMI with 5% BSA in the presence of histamine (ranging from 1.25-20 µM) was added to the bottom chamber. To test the various histamine receptor antagonists 10 µM of the test compounds were added to the top and bottom chambers. Eosinophils were added to the top chamber whereas histamine or chemotactic factors were placed in the lower chamber. The plates were incubated for 3 h at 37° C. Transwells were removed and the number of cells in the bottom chamber were counted for 60 s using a flow cytometer, or were quantitated by using Giemsa staining.

Inhibition of Mast Cell Chemotaxis by $H_4$ Receptor Antagonist in an Animal Model of Asthma and Allergic Rhinitis An animal model was used to test the observation that mast cells accumulate in response to allergic inflammation and that this accumulation can be blocked by $H_4$ receptor antagonists. Compounds of the present invention were tested in this model to demonstrate their use as treatments for allergic rhinitis or asthma. Mice were sensitized by intraperitoneal injection of ovalbumin/Alum (10 µg in 0.2 ml $Al(OH)_3$, 2%) on Day 0 and Day 14. On Day 21 through 23 mice were challenged by PBS or ovalbumin, and sacrificed 24 h after the last challenge on Day 24. A section of the trachea was removed and fixed in formalin. Paraffin embedding and longitudinal sectioning of tracheas were performed followed by staining of mast cells with toluidine blue. Alternatively, trachea were frozen in OCT for frozen sectioning, and mast cells were identified by IgE staining. Mast cells were quantified as sub-mucosal or sub-epithelial depending on their location within each tracheal section. Exposure to allergen should increase the number of sub-epithelial mast cells, and this effect is blocked by $H_4$ receptor antagonists.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. These other embodiments are also within the scope of the invention.

What is claimed is:

1. A compound of formula (II):

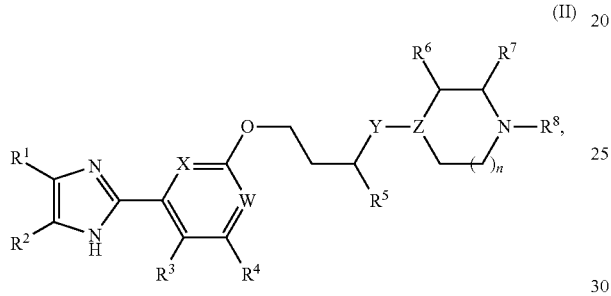

wherein
- W is, independently from other member and substituent assignments, $CR^9$;
- X is, independently from other member and substituent assignments, $CR^9$;
- Y is, independently from other member and substituent assignments, O, $NR^{10}$ or $CR^{10}R^{11}$;
- Z is, independently from other member and substituent assignments, $CR^{12}$;
- n is, independently from other member and substituent assignments, 1;
- each of $R^{1-2}$ is, independently from other member and substituent assignments, —H, —$CF_3$, —$C_{1-6}$alkyl, —$C_{3-6}$cycloalkyl, optionally substituted aryl or optionally substituted heteroaryl; or, $R^1$ and $R^2$ taken together with the carbon atoms to which they are attached form a cyclic structure Cyc1 selected from 5- or 6-membered carbocycle, and 5- or 6-membered heterocycle with 1 heteroatom, wherein said cyclic structure Cyc1 is, independently from other substituent assignments, substituted with 0, 1, or 2 substituents selected from —$C_{1-3}$alkyl, halo, hydroxy, amino, and —$C_{1-3}$alkoxy;
- each of $R^{3-4}$ and $R^9$ is, independently from other member and substituent assignments, —H, —$C_{1-6}$alkyl, halo, —$CF_3$, —$OCF_3$, —$OR^c$, —$SR^c$, —$S(O)R^c$, —$SO_2R^c$, $C_{1-4}$alkoxy, cyano, nitro, —$C(O)NR^aR^b$, —$C(O)$phenyl, —$C(O)C_{1-6}$alkyl, —$S(O)C_{1-4}$alkyl, or —$SO_2C_{1-4}$alkyl; or, $R^3$ and $R^4$ taken together with the carbon atoms to which they are attached form a cyclic structure Cyc2 selected from aryl, 5- or 6-membered carbocycle, and 5- or 6-membered heterocycle with 1 or 2 heteroatoms, wherein said cyclic structure Cyc2 is, independently from other substituent assignments, substituted with 0, 1, or 2 substituents selected from —$C_{1-3}$alkyl, halo, hydroxy, amino, and —$C_{1-3}$alkoxy; wherein each of $R^a$, $R^b$ and $R^c$ is, independently from other substituent assignments, selected from H, $C_{1-4}$alkyl, $C_{3-6}$cycloalkyl, phenyl, $(C_{3-6}$cycloalkyl$)C_{1-2}$alkyl-, benzyl and phenethyl, or $R^a$ and $R^b$ taken together with the nitrogen to which they are attached, form a 4-7 membered heterocyclic ring HetCyc1, wherein said ring HetCyc1 has 0 or 1 additional heteroatoms selected from O, S, >NH and >$NC_{1-6}$alkyl, and wherein any phenyl, phenethyl, benzyl, alkyl or cycloalkyl moiety in any of said $R^{1-4}$, $R^a$, $R^b$, $R^c$, and said ring HetCyc1 is optionally, and independently from other substituent assignments, substituted with 1, 2 or 3 substituents selected from $C_{1-3}$alkyl, halo, hydroxy, amino, and $C_{1-3}$alkoxy;
- $R^5$ is, independently from other member and substituent assignments, —H, —$C_{1-6}$alkyl, —$C_{1-4}$alkoxy, or hydroxy;
- each of $R^6$ and $R^7$ is, independently from other member and substituent assignments, —H or —$C_{1-6}$alkyl;
- $R^8$ is, independently from other member and substituent assignments, —H or —$C_{1-4}$alkyl;
- each of $R^{10}$ and $R^{11}$ is, independently from other member and substituent assignments, —H or —$C_{1-4}$alkyl; or when Y is $CR^{10}R^{11}$, $R^{10}$ and $R^{11}$ taken together with the carbon member to which they are attached form an optionally substituted cyclic structure Cyc4, wherein said cyclic structure Cyc4 is a 3- to 6-membered carbocycle or a 3- to 6-membered non-aromatic heterocycle with 0 or 1 additional heteroatoms, or $CR^{10}R^{11}$ is C=O;
- $R^{12}$ is, independently from other member and substituent assignments, —H, —$C_{1-4}$alkyl, hydroxy, or —$C_{1-4}$alkoxy;
- an enantiomer, diastereomer, racemate thereof, or a pharmaceutically acceptable salt, amide or ester thereof;
- with the following provisos:
  - when Y is O or $NR^{10}$, then Z is $CR^{12}$ and $R^5$ is not hydroxy or —$C_{1-4}$alkoxy;
  - when $R^1$ and $R^2$ are both —H, Y is $CH_2$, and $R^8$ is methyl, then $R^5$ is not hydroxyl.

2. A compound of claim 1, wherein Y is $CR^{10}R^{11}$.

3. A compound of claim 1, wherein Y is $CH_2$.

4. A compound of claim 1, wherein one or both of $R^1$ and $R^2$ are a mono- or di-substituted phenyl ring.

5. A compound of claim 1, wherein only one of $R^1$ or $R^2$ is a mono-substituted phenyl ring.

6. A compound of claim 1, wherein $R^3$ is H, F, Cl, methyl, or ethyl.

7. A compound of claim 1, wherein $R^3$ is F, Cl, or methyl.

8. A compound of claim 1, wherein $R^3$ is Cl or methyl.

9. A compound of claim 1, wherein $R^4$ is H, F, Cl, or methyl.

10. A compound of claim 1, wherein $R^5$ is H, methyl, or hydroxy.

11. A compound of claim 1, wherein $R^5$ is H.

12. A compound of claim 1, wherein $R^6$ and $R^7$ are, independently, selected from the group consisting of
   a) H, and
   b) methyl, ethyl, propyl, and isopropyl.

13. A compound of claim 1, wherein $R^6$ and $R^7$ are, independently, H or methyl.

14. A compound of claim 1, wherein $R^8$ is H, methyl, or ethyl.

15. A compound of claim 1, wherein $R^8$ is methyl.

16. A compound of claim 1, wherein $R^9$ is H, F, Cl, or methyl.

17. A compound selected from:
   4-(4-{3-[4-(4-Chloro-phenyl)-5-methyl-1H-imidazol-2-yl]-phenoxy}-butyl)-1-methyl-piperidine;
   1-Methyl-4-{4-[3-(4-phenyl-5-trifluoromethyl-1H-imidazol-2-yl)-phenoxy]-butyl}-piperidine;
   1-Methyl-4-(4-{3-[5-methyl-4-(4-trifluoromethyl-phenyl)-1H-imidazol-2-yl]-phenoxy}-butyl)-piperidine;
   2-{3-[4-(1-Methyl-piperidin-4-yl)-butoxy]-phenyl}-3H-imidazo[4,5-b]pyridine;
and pharmaceutically acceptable salts thereof.

18. A pharmaceutical composition, comprising at least one compound as claimed in claim 1.

19. A pharmaceutical composition, comprising at least one compound as claimed in claim 2.

20. A pharmaceutical composition, comprising at least one compound as claimed in claim 3.

21. A pharmaceutical composition, comprising at least one compound as claimed in claim 4.

22. A pharmaceutical composition, comprising at least one compound as claimed in claim 5.

23. A pharmaceutical composition, comprising at least one compound as claimed in claim 6.

24. A pharmaceutical composition, comprising at least one compound as claimed in claim 7.

25. A pharmaceutical composition, comprising at least one compound as claimed in claim 8.

26. A pharmaceutical composition, comprising at least one compound as claimed in claim 9.

27. A pharmaceutical composition, comprising at least one compound as claimed in claim 10.

28. A pharmaceutical composition, comprising at least one compound as claimed in claim 11.

29. A pharmaceutical composition, comprising at least one compound as claimed in claim 12.

30. A pharmaceutical composition, comprising at least one compound as claimed in claim 13.

31. A pharmaceutical composition, comprising at least one compound as claimed in claim 14.

32. A pharmaceutical composition, comprising at least one compound as claimed in claim 15.

33. A pharmaceutical composition, comprising at least one compound as claimed in claim 16.

34. A pharmaceutical composition, comprising at least one compound as claimed in claim 17.

* * * * *